United States Patent
Chin

(10) Patent No.: US 11,491,234 B2
(45) Date of Patent: Nov. 8, 2022

(54) MITOCHONDRIAL LOCALIZATION SIGNALS IN HUMAN TAFAZZIN AND USES THEREOF

(71) Applicant: University of Washington, Seattle, WA (US)

(72) Inventor: Michael T. Chin, Seattle, WA (US)

(73) Assignee: University of Washington, Seattle, WA (US)

(*) Notice: Subject to any disclaimer, the term of this patent is extended or adjusted under 35 U.S.C. 154(b) by 291 days.

(21) Appl. No.: 16/762,897

(22) PCT Filed: Nov. 9, 2018

(86) PCT No.: PCT/US2018/060168
§ 371 (c)(1),
(2) Date: May 8, 2020

(87) PCT Pub. No.: WO2019/094823
PCT Pub. Date: May 16, 2019

(65) Prior Publication Data
US 2021/0170042 A1  Jun. 10, 2021

Related U.S. Application Data

(60) Provisional application No. 62/583,900, filed on Nov. 9, 2017.

(51) Int. Cl.
*A61K 47/64*  (2017.01)
*A61K 47/65*  (2017.01)
*A61K 38/44*  (2006.01)

(52) U.S. Cl.
CPC ............. *A61K 47/64* (2017.08); *A61K 38/44* (2013.01); *A61K 38/446* (2013.01); *A61K 47/65* (2017.08)

(58) Field of Classification Search
CPC ...... A61K 47/64; A61K 38/44; A61K 38/446; A61K 47/65
See application file for complete search history.

(56) References Cited

U.S. PATENT DOCUMENTS

2006/0257942 A1  11/2006  Waldo et al.
2015/0203827 A1  7/2015  Chin et al.

OTHER PUBLICATIONS

Sahdeo Prasad, Age-Associated Chronic Diseases Require Age-Old Medicine: Role of Chronic Inflammation, Prev Med. May 2012 ; 54(Suppl): S29-S37. doi: 10.1016/j.ypmed.2011.11.011.*
Hyun Jun Jung, Biological activity of Tat (47-58) peptide on human pathogenic fungi, Biochemical and Biophysical Research Communications 345 (2006) 222-228.*
Bione, Silvia et al., "A novel X-linked gene, G4.5. is responsible for Barth syndrome," Nature Genetics, 12(4):385-389, 1996.
Vreken, Peter et al., "Defective Remodeling of Cardiolipin and Phosphatidylglycerol in Barth syndrome," Biochemical Biophysical Research Communications 279(2):378-382, 2000.
Gonzalez, Iris L., "Barth Syndrome: TAZ Gene Mutations, mRNAs, and Evolution", American Journal of Medical Genetics, 134A(4):409-414, 2005.
Kirwin, Susan M. et al., "Tafazzin splice variants and mutations in Barth syndrome", Molecular Genetics and Metabolism, 111(1):26-32, 2014.
Xu, Yang et al., "The Enzymatic Function of Tafazzin," The Journal of Biological Chemistry, 281(51):39217-39224, 2006.
Houtkooper, Riekelt H., et al., "The enigmatic role of tafazzin in cardiolipin metabolism," Biochimica et Biophysica Acta, 1788(10):2003-2014, 2009.
Schlame, Michael, "Cardiolipin synthesis for the assembly of bacterial and mitochondrial membranes," Journal of Lipid Research, 49(8):1607-1620, 2008.
Schlame, Michael et al., "The physical state of lipid substrates provides transacylation specificity for tafazzin," Nature Chemical Biology, 8(10):862-869, 2012.
E. Mileykovskaya et al., "Cardiolipin in Energy Transducing Membranes," Biochemistry (Moscow), 70(2):154-158, 2005.
Schlame, Michael et al., "Deficiency of Tetralinoleoyl-Cardiolipin in Barth Syndrome," Ann Neurol, 51(5)634-637, 2002.
Friedman, Jonathan R. et al., "MICOS coordinates with respiratory complexes and lipids to establish mitochondrial inner membrane architecture," eLife, 2015, 25 pages.
Pfeiffer, Kathy et al., "Cardiolipin Stabilizes Respiratory Chain Supercomplexes," The Journal of Biological Chemistry, 278(52):52873-52880, 2003.
Chan, David C., "Mitochondria: Dynamic Organelles in Disease, Aging, and Development," Cell, 125(7):1241-1252, 2006.
Dudek, Jan, "Role of Cardiolipin in Mitochondrial Signaling Pathways," Frontiers in Cell and Developmental Biology, 5 (90), 2017, 17 pages.
Herndon, Jenny D. et al.,"The Tazlp Transacylase is Imported and Sorted into the Outer Mitochondrial Membrane via a Membrane Anchor Domain," Eukaryotic Cell, 12(12):1600-1608, 2013.

(Continued)

*Primary Examiner* — Julie Ha
*Assistant Examiner* — Erinne R Dabkowski
(74) *Attorney, Agent, or Firm* — Christensen O'Connor Johnson Kindness PLLC

(57) ABSTRACT

Pharmaceutical compositions including a mitochondria-targeting polypeptide and a therapeutic agent coupled to the mitochondria-targeting polypeptide are provided. Methods of treating a subject in need thereof including administering a therapeutically effective amount of the pharmaceutical composition to the subject are provided. The subject may have an aging-related condition, heart failure, diabetes, myocardial infarction, acquired mitochondrial disorder, and/or inherited mitochondrial disorder. Methods of delivering compound to a mitochondrion and of preparing a compound for delivery to a mitochondrion are also provided. Furthermore, biological tracers including a mitochondria-targeting polypeptide and a label coupled to the mitochondria-targeting polypeptide are provided.

14 Claims, 9 Drawing Sheets
Specification includes a Sequence Listing.

(56) References Cited

OTHER PUBLICATIONS

El-Hattab, Ayman W. et al., "Mitochondrial Cardiomyopathies," Frontiers in Cardiovascular Medicine, 3(25), 2016, 9 pages.
Klapoetke, Nathan C. et al., "Independent optical excitation of distinct neural populations," Nature Methods 11 (3):338-346, 2014.
Tsai, Shengdar Q. et al., "Dimeric CRISPR RNA-guided FokI nucleases for highly specific genome editing," Nature Biotechnology, 32(6):569-576, 2014.
Lu, Ya-Wen et al., "Defining functional classes of Barth syndrome mutation in humans," Human Molecular Genetics, 25 (9):1754-1770, 2016.
Xu, Yang et al., "Characterization of Tafazzin Splice Variants from Humans and Fruit Flies," The Journal of Biological Chemistry, 284(42):29230-9, 2009.
Hijikata, Atsushi et al., "Structural and functional analyses of Barth syndrome-causing mutations and alternative splicing in the tafazzin acyltransferase domain," Meta Gene 4:92-106, 2015.
Chacinska, Agnieszka et al., "Importing Mitochondrial Proteins: Machineries and Mechanisms," Cell, 138(4):628-44, 2009.
Dudek, Jan et al., "Mitochondrial protein import: Common principles and physiological networks," Biochimica et Biophysica Acta, 1833(2):274-85, 2013.
Stojanovski, Diana et al., "The MIA system for protein import into the mitochondrial intermembrane space," Biochimica et Biophysica Acta, 1783(4):610-7, 2008.
Whited, Kevin et al., "Seven functional classes of Barth syndrome mutation," Human Molecular Genetics, 22 (3):483-92, 2013.
Abe, Yoshito et al., "Structural Basis of Presequence Recognition by the Mitochondrial Protein Import Receptor Tom20," Cell, 100(5):551-60, 2000.
Neupert, Walter et al., "Translocation of Proteins into Mitochondria," The Annual Review of Biochemistry, 76:723-49, 2007.
Acehan, Devrim et al., "Cardiolipin Affects the Supramolecular Organization of ATP Synthase in Mitochondria," Biophysical Journal, 100(9):2184-92, 2001.
Chacinska, Agnieszka et al., "Mitochondrial Presequence Translocase: Switching between TOM Tethering and Motor Recruitment Involves Tim21 and Tim17," Cell, 120(6):817-29, 2005.
Harner, Max et al., "Lateral release of proteins from the TOM complex into the outer membrane of mitochondria," The EMBO Journal, 30(16):3232-41, 2011.
Sugiura, Ayumu et al., "A new pathway for mitochondrial quality control: mitochondrial-derived vesicles," The EMBO Journal, 33(19):2142-56, 2014.
Mohanty, Abhishek et al., "Emerging roles of mitochondria in the evolution, biogenesis, and function of peroxisomes," Frontiers in Physiology, 4(268), 2013, 12 pages.
Wriessnegger, Tamara et al., "Lipid composition of peroxisomes from the yeast Pichia pastoris grown on different carbon sources," Biochimica et Biophysica Acta, 1771 (4):455-61, 2007.
Settembre, Carmine et al., "Signals from the lysosome: a control center for cellular clearance and energy metabolism," Nat Rev Mol Cell Biol, 14(5):283-96, 2013.
Dhillon, Varinderpal S. et al., "Mutations that affect mitochondrial functions and their association with neurodegenerative diseases," Mutation Research/Reviews in Mutation Research, 759:1-13, 2014.
Wisnovsky, Simon et al., "Mitochondrial Chemical Biology: New Probes Elucidate the Secrets of the Powerhouse of the Cell," Cell Chemical Biology, 23(8):917-927, 2016.
Cerrato, Carmine Pasquale et al., "Effect of a Fusion Peptide by Covalent Conjugation of a Mitochondrial Cell-Penetrating Peptide and a Glutathione Analog Peptide," Molecular Therapy: Methods and Clinical Development, 5:221-231,2017.
Yu-Wai-Man, P. et al., "Treatment strategies for inherited optic neuropathies: past, present and future," Eye, 28 (5):521-537, 2014.
Pilz, Yasmine L. et al., "A Review of Mitochondrial Optic Neuropathies: From Inherited to Acquired Forms," Journal of Optometry, 10(4):205-214, 2016.
International Search Report, dated Apr. 19, 2019, for International Patent Application No. PCT/US2018/060168. (5 pages).
Written Opinion of the International Searching Authority, dated Apr. 19, 2019, for International Patent Application No. PCT/US2018/060168. (10 pages).
International Preliminary Report on Patentability, dated May 12, 2020, for International Patent Application No. PCT/US2018/060168. (11 pages).

\* cited by examiner

```
          10         20         30         40         50
MPLHVKWPFP AVPPLTWTLA SSVVMGLVGT YSCFWTKYMN HLTVHNREVL
          60         70         80         90        100
YELIEKRGPA TPLITVSNHQ SCMDDPHLWG ILKLRHIWNL KLMRWTPAAA
         110        120        130        140        150
DICFTKELHS HFFSLGKCVP VCRGAEFFQA ENEGKGVLDT GRHMPGAGKR
         160        170        180        190        200
REKGDGVYQK GMDFILEKLN HGDWVHIFPE GKVNMSSEFL RFKWGIGRLI
         210        220        230        240        250
AECHLNPIIL PLWHVGMNDV LPNSPPYFPR FGQKITVLIG KPFSALPVLE
         260        270        280        290
RLRAENKSAV EMRKALTDFI QEEFQHLKTQ AEQLHNHLQP GR (SEQ ID NO: 45)
```

FIG. 9

MITOCHONDRIAL LOCALIZATION SIGNALS IN HUMAN TAFAZZIN AND USES THEREOF

CROSS-REFERENCE TO RELATED APPLICATIONS

This application is a national phase entry of International Application No. PCT/US2018/060168, filed Nov. 9, 2018, which claims the benefit of U.S. Provisional Application No. 62/583,900, filed Nov. 9, 2017, both of which are hereby incorporated by reference in their entirety.

TECHNICAL FIELD

The present disclosure relates generally to pharmaceutical compositions including a mitochondria-targeting polypeptide and a therapeutic agent coupled to the mitochondria-targeting polypeptide. The present disclosure also relates to methods of treating a subject in need thereof including administering a therapeutically effective amount of the pharmaceutical composition to the subject. The subject may have an aging-related condition, heart failure, diabetes, myocardial infarction, acquired mitochondrial disorder, and/or inherited mitochondrial disorder. The present disclosure also relates to methods of delivering a compound to a mitochondrion and of preparing a compound for delivery to a mitochondrion. Furthermore, the present disclosure relates to biological tracers including a mitochondria-targeting polypeptide and a label coupled to the mitochondria-targeting polypeptide.

BACKGROUND

Barth syndrome is an X-linked recessive disorder that presents clinically with 3-methylglutaconic aciduria, neutropenia, hypotonia, and cardiomyopathy. Causative genetic mutations have been mapped to the tafazzin (TAZ) gene, which encodes a phospholipid transacylase that regulates the maturation of cardiolipin (CL) (S. Bione, et al., Nat Genet 12(4) (1996) 385-9 and P. Vreken, F. et al., Biochem Biophys Res Commun 279(2) (2000) 378-82). The TAZ gene lies on the short arm of chromosome X and is encoded by 11 exons. Four splice variants have been identified and validated: full length (TAZ FL), a variant lacking exon 5 (TAZ Δ5), one lacking exon 7 (TAZ Δ7) and one variant lacking both exon 5 and exon 7 (TAZ Δ5Δ7). Studies show that although all four variants localize to mitochondria, only the former two have transacylase activity, with TAZ Δ5 being predominant. TAZ FL is present only in primates, whereas TAZ Δ5 is highly conserved (I. L. Gonzalez, Am J Med Genet A 134(4) (2005) 409-14 and S. M. Kirwin, et al., Mol Genet Metab 111(1) (2014) 26-32).

While the function of the non-enzymatically active isoforms of TAZ has yet to be determined, TAZ FL and TAZ Δ5 catalyze the final maturation step of the ubiquitous mitochondrial phospholipid, CL (Y. Xu, The Journal of biological chemistry 281(51) (2006) 39217-24 and R. H. Houtkooper, et al., Biochim Biophys Acta 1788(10) (2009) 2003-14). TAZ is localized to mitochondrial membranes in mammals, where it acts by exchanging acyl chains between CL and other phospholipids, the final result being a CL molecule with predominantly unsaturated fatty acyl chains (M. Schlame, J Lipid Res 49(8) (2008) 1607-20). It has been postulated that TAZ activity is promiscuous and the observed specificity of its action is conferred by the restraints of the membrane space where it is most active (M. Schlame, et al., Nat Chem Biol 8(10) (2012) 862-9).

CL is a unique phospholipid that is exclusively synthesized and functions in mitochondrial membranes (M. Schlame, et al., J Lipid Res 49(8) (2008) 1607-20 and E. Mileykovskaya, et al., Biochemistry (Mosc) 70(2) (2005) 154-8). It consists of a diphosphatidylglycerol molecule that binds four acyl chains. TAZ remodels CL by exchanging its initially saturated acyl chains for unsaturated acyl chains, making the molecule more thermodynamically favorable for membranes with a high degree of curvature (M. Schlame, D. et al., Nat Chem Biol 8(10) (2012) 862-9). Tetralinoleoyl CL (L4CL) is the most abundant mature species in mammalian muscle. In BTHS patient tissues, mature CL species are decreased and the immature monolysocardiolipin (MLCL), a CL molecule with only three acyl chains, accumulates (M. Schlame, et al., Ann Neurol 51(5) (2002) 634-7), CL interacts with protein complexes involved in the formation and maintenance of mitochondrial inner membrane cristae, as well as with respiratory supercomplexes in the inner mitochondrial membrane (IMM) (J. R. Friedman, et al., MICOS coordinates with respiratory complexes and lipids to establish mitochondrial inner membrane architecture, Elife 4 (2015) and K. Pfeiffer, et al., J Biol Chem 278(52) (2003) 52873-80). Failure to properly remodel CL ultimately results in defects of mitochondrial morphology and function, both of which have been implicated in cardiovascular disease by numerous studies (D. C. Chan, Cell 125(7) (2006) 1241-52 and J. Dudek, Front Cell Dev Biol 5 (2017) 90).

Critically, as CL is only synthesized in mitochondria, correct targeting of TAZ must occur in order for CL to undergo its final step of remodeling. Previous work in yeast has identified a 28 amino acid peptide in the C-terminus of the TAZ that is necessary for mitochondrial targeting. However, the exact mitochondrial targeting sequence for human TAZ is yet unknown (J. D. Herndon, et al., Eukaryot Cell 12(12) (2013) 1600-8).

BRIEF DESCRIPTION OF THE DRAWINGS

The embodiments disclosed herein will become more fully apparent from the following description and appended claims, taken in conjunction with the accompanying drawings.

FIG. 9 is the amino acid sequence of TAZ.

DETAILED DESCRIPTION

Figure 1:
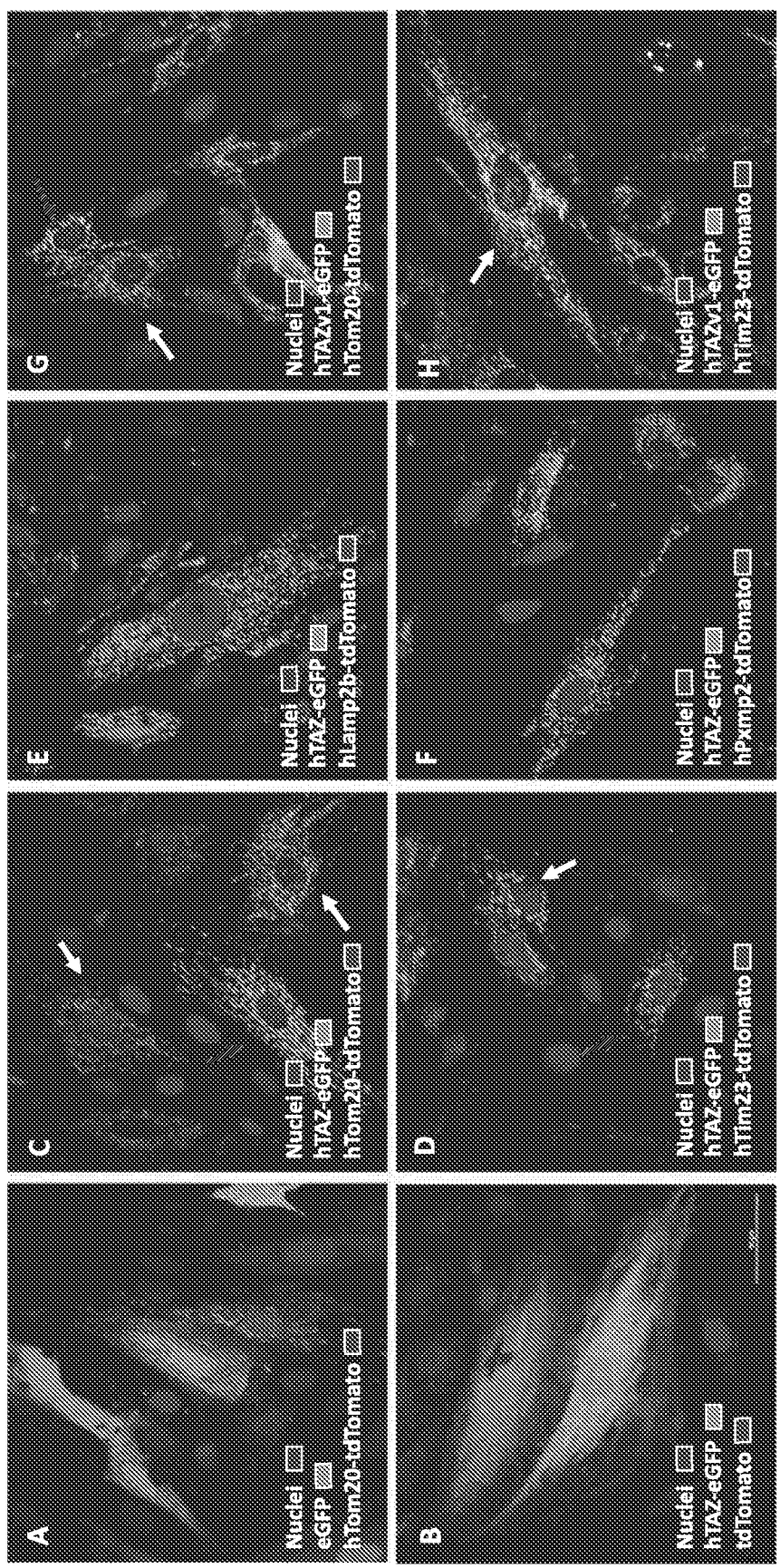
FIG. 1 shows mitochondrial localization of human tafazzin isoforms in rat cardiomyoblast H9c2 cells. The H9c2 cells were transfected with EGFP and tdTomato native and fusion protein expression plasmids and fixed with 4% paraformaldehyde 24 hours after transfection and photographed with a confocal microscope with a 60× oil objective lens. The maximal intensity projection of z-stack images are shown for the co-expression of hTAZ isoform 1 and 2 with organelle markers. Panel A, eGFP and mitochondrial outer membrane marker hTom20-tdTomato; panel B, TAZ isoform 2 hTAZ-eGFP and tdTomato; panel C, hTAZ-eGFP and mitochondrial outer membrane hTom20-tdTomato; panel D, hTAZ-eGFP and hTim23-tdTomato; panel E, hTAZ-eGFP and lysosomal hLamp2b-tdTomato; panel F, hTAZ-eGFP and peroxisome hPxmp2-tdTomato; panel G, TAZ isoform 1 hTAZv1-eGFP and hTom20-tdTomato; panel H, hTAZv1-eGFP and hTim23-tdTomato. Cells showing mitochondrial localization of hTAZ-eGFP with mitochondrial markers are indicated by white arrows and cells in which tdTomato is more strongly expressed are indicated by patterned arrows. All images were taken with a 60× oil lens and the white bar in panel B represents 50 μm.

The present disclosure relates generally to pharmaceutical compositions including a mitochondria-targeting polypeptide and a therapeutic agent coupled to the mitochondria-targeting polypeptide. The present disclosure also relates to methods of treating a subject in need thereof. The method may include administering a therapeutically effective amount of the pharmaceutical composition to the subject. The subject may have an aging-related condition, heart failure, diabetes, myocardial infarction, acquired mitochondrial disorder, and/or inherited mitochondrial disorder. The present disclosure also relates to methods of delivering a compound to a mitochondrion and methods of preparing a compound for delivery to a mitochondrion. Biological tracers including a mitochondria-targeting polypeptide and a label coupled to the mitochondria-targeting polypeptide are also provided.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, "tafazzin" refers to a phospholipid-lysophospholipid transacylase that can be responsible for modification of cardiolipin (a membrane phospholipid) to its tetralinoleoyl form. In some embodiments, tafazzin can refer to full-length human tafazzin or human tafazzin lacking exon 5, both of which exhibit transacylase activity. In certain embodiments, tafazzin can refer to full-length mouse tafazzin, which is homologous to the human tafazzin lacking exon 5.

As used herein, "peptide" and "polypeptide" are used in their broadest senses to refer to a sequence of subunit amino acids. The peptides or polypeptides of the invention may comprise L-amino acids, D-amino acids (which can be resistant to L-amino acid-specific proteases in vivo), or a combination of D- and L-amino acids. The terms peptide and polypeptide can be used interchangeably. The peptides and polypeptides described herein may be chemically synthesized or recombinantly expressed. The peptides and polypeptides may be linked to any other moiety as deemed useful for a given purpose. Such linkage can comprise covalent linkages or non-covalent linkages as is understood by those of skill in the art.

As used herein, "fusion proteins" or "chimeric proteins" refer to proteins created through the joining of two or more genes (e.g., a fusion gene), each of which originally coded for separate proteins. Translation of this fusion gene may result in one or more polypeptides comprising functional properties derived from each of the two or more genes.

As used herein, a "cellular permeability peptide" is a peptide that facilitates cellular uptake of the peptide itself and other peptides that are linked to the cellular permeability peptide. In certain embodiments, these peptides can comprise portions of *Drosophila* antennapedia, HIV Tat, cardiac targeting, and Kaposi FGF4 peptides, which may facilitate cellular uptake. As used herein, such peptide fragments may be referred to as antennapedia permeability peptides, HIV Tat permeability peptides, cardiac targeting permeability peptides, and Kaposi FGF4 permeability peptides.

Amino acid residues as disclosed herein can be modified by conservative substitutions to maintain, or substantially maintain, overall polypeptide structure and/or function. As used here, "conservative amino acid substitution" indicates that: hydrophobic amino acids (i.e., Ala, Cys, Gly, Pro, Met, Sce, Sme, Val, Ile, and Leu) can be substituted with other hydrophobic amino acids; hydrophobic amino acids with bulky side chains (i.e., Phe, Tyr, and Trp) can be substituted with other hydrophobic amino acids with bulky side chains; amino acids with positively charged side chains (i.e., Arg, His, and Lys) can be substituted with other amino acids with positively charged side chains; amino acids with negatively charged side chains (i.e., Asp and Glu) can be substituted with other amino acids with negatively charged side chains; and amino acids with polar uncharged side chains (i.e., Ser, Thr, Asn, and Gln) can be substituted with other amino acids with polar uncharged side chains.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul, et al. (1997) "Gapped BLAST and PSI-BLAST: a new generation of protein database search programs," Nucleic Acids Res. 25:3389-3402, with the parameters set to default values.

The state of the art includes various methods that may be used to align two given nucleic acid or amino acid sequences and to calculate the degree of identity (see, e.g., Arthur Lesk (2008), Introduction to bioinformatics, Oxford University Press, 2008, 3rd edition). In some embodiments, the ClustalW software can be used using default settings (Larkin, M. A., et al. (2007). Clustal W and Clustal X version 2.0. Bioinformatics, 23, 2947-2948). As understood in the art, "similarity" between two polypeptides is determined by comparing the amino acid sequence and conserved amino acid substitutes thereto of the polypeptide to the sequence of a second polypeptide (e.g., using GENEWORKS™, Align, the BLAST algorithm, or other algorithms described herein and practiced in the art).

Treating a subject can comprise delivering an effective amount or delivering a prophylactic treatment and/or a therapeutic treatment to a subject (e.g., a patient). An "effective amount" is an amount of a compound that can result in a desired physiological change in a subject. Effective amounts may also be administered for research purposes.

A "prophylactic treatment" comprises a treatment administered to a subject who does not display signs or symptoms of a disease or condition, or a subject who displays only early signs or symptoms of a disease or condition, such that treatment is administered for the purpose of diminishing, preventing, and/or decreasing the risk of further developing the disease or condition or of diminishing, preventing, and/or decreasing the risk of developing the disease or condition. Thus, a prophylactic treatment may function as a preventative treatment against a disease or condition.

A "therapeutic treatment" comprises a treatment administered to a subject who displays symptoms or signs of a disease or a condition and the therapeutic treatment is administered to the subject for the purpose of diminishing or eliminating the symptoms or the signs of the disease or the condition.

"Therapeutically effective amounts" comprise amounts that provide prophylactic treatment and/or therapeutic treatment. Therapeutically effective amounts need not fully prevent or cure the disease or the condition but can also provide a partial benefit, such as a delay of onset or an alleviation or an improvement of at least one symptom of the disease or the condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the $IC_{50}$ as determined in cell culture. Such information can be used to more accurately determine useful doses in subjects of interest.

The actual dose amount administered to a particular subject can be determined by a physician, a veterinarian, or a researcher, taking into account parameters such as, but not limited to, physical and physiological factors including body weight, severity of condition, type of disease, previous or concurrent therapeutic interventions, idiopathy of the subject, and/or route of administration.

Doses can range from 0.1 mg/kg/day to 5 mg/kg/day, from 0.5 mg/kg/day to 1 mg/kg/day, from 0.1 mg/kg/day to 5 µg/kg/day, or from 0.5 mg/kg/day to 1 µg/kg/day. In other non-limiting examples, a dose can comprise 1 µg/kg/day, 5 µg/kg/day, 10 µg/kg/day, 50 µg/kg/day, 100 µg/kg/day, 200 µg/kg/day, 350 µg/kg/day, 500 µg/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day, or 1000 mg/kg/day. Therapeutically effective amounts can be achieved by administering single or multiple doses during the course of a treatment regimen (i.e., days, weeks, months, etc.).

In some embodiments, at least one compound is provided as part of a pharmaceutical composition. The pharmaceutical composition can comprise, for example, at least 0.1% w/v of a compound. In other embodiments, the pharmaceutical composition can comprise between 2% and 75% of compound per weight of the pharmaceutical composition, or between 25% and 60% of compound per weight of the pharmaceutical composition.

Pharmaceutically acceptable salts, tautomers, and isomers of the compounds disclosed herein can also be used. Exemplary salts can include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The formulations described herein can be administered by, without limitation, injection, inhalation, infusion, perfusion, lavage, and/or ingestion. Routes of administration can include, but are not limited to, intravenous, intradermal, intraarterial, intraperitoneal, intralesional, intracranial, intraarticular, intraprostatic, intrapleural, intratracheal, intranasal, intravitreal, intravaginal, intrarectal, topical, intratumoral, intramuscular, intravesicular, intrapericardial, intraumbilical, intraocularal, mucosal, oral, subcutaneous, and/or subconjunctival.

In some embodiments, for injection, formulations can be made as aqueous solutions, such as in buffers including, but not limited to, Hanks' solution, Ringer's solution, and/or physiological saline. The solutions can contain formulatory agents such as suspending, stabilizing, and/or dispersing agents. Alternatively, the formulation can be in lyophilized and/or powder form for constitution with a suitable vehicle control (e.g., sterile pyrogen-free water) before use.

Any formulation disclosed herein can advantageously comprise any other pharmaceutically acceptable carrier or carriers, which comprise those that do not produce significantly adverse, allergic, or other untoward reactions that may outweigh the benefit of administration, whether for research, prophylactic, and/or therapeutic treatments. Exemplary pharmaceutically acceptable carriers and formulations are disclosed in Remington's Pharmaceutical Sciences, 18th Ed., Mack Printing Company, 1990, which is incorporated by reference herein for its teachings regarding the same. Moreover, formulations can be prepared to meet sterility, pyrogenicity, general safety, and purity standards as required by the United States FDA's Division of Biological Standards and Quality Control and/or other relevant U.S. and foreign regulatory agencies.

Exemplary, generally used, pharmaceutically acceptable carriers may comprise, but are not limited to, bulking agents or fillers, solvents or co-solvents, dispersion media, coatings, surfactants, antioxidants (e.g., ascorbic acid, methionine, and vitamin E), preservatives, isotonic agents, absorption delaying agents, salts, stabilizers, buffering agents, chelating agents (e.g., EDTA), gels, binders, disintegration agents, and/or lubricants.

Exemplary buffering agents may comprise, but are not limited to, citrate buffers, succinate buffers, tartrate buffers, fumarate buffers, gluconate buffers, oxalate buffers, lactate buffers, acetate buffers, phosphate buffers, histidine buffers, and/or trimethylamine salts.

Exemplary preservatives may comprise, but are not limited to, phenol, benzyl alcohol, meta-cresol, methylparaben, propyl paraben, octadecyldimethylbenzyl ammonium chloride, benzalkonium halides, hexamethonium chloride, alkyl parabens (such as methyl or propyl paraben), catechol, resorcinol, cyclohexanol, and/or 3-pentanol.

Exemplary isotonic agents may comprise polyhydric sugar alcohols comprising, but not limited to, trihydric or higher sugar alcohols, (e.g., glycerin, erythritol, arabitol, xylitol, sorbitol, and/or mannitol).

Exemplary stabilizers may comprise, but are not limited to, organic sugars, polyhydric sugar alcohols, polyethylene glycol, sulfur-containing reducing agents, amino acids, low molecular weight polypeptides, proteins, immunoglobulins, hydrophilic polymers, and/or polysaccharides.

Formulations can also be depot preparations. In some embodiments, such long-acting formulations may be administered by, without limitation, implantation (e.g., subcutaneously or intramuscularly) or by intramuscular injection. Thus, for example, compounds can be formulated with suitable polymeric and/or hydrophobic materials (e.g., as an emulsion in an acceptable oil) or ion exchange resins, or as sparingly soluble derivatives (e.g., as a sparingly soluble salt).

Additionally, in various embodiments, compounds can be delivered using sustained-release systems, such as semipermeable matrices of solid polymers comprising at least one compound. Various sustained-release materials have been established and are well known by those of ordinary skill in the art. Sustained-release capsules may, depending on their chemical nature, release the compound following administration for a few weeks up to over 100 days.

To identify intrinsic mitochondrial localization sequences in the human TAZ protein, sequential TAZ peptide-eGFP fusion protein expression constructs were made and the localization of eGFP fluorescence by confocal microscopy was analyzed. These fusion proteins were assessed for mitochondrial localization through cotransfection of H9c2 cells with plasmids encoding organellar markers linked to TdTomato. Two peptides of TAZ have been identified that are independently responsible for mitochondrial localization. Using CRISPR-generated TAZ knock out cell lines, it was found that these peptides are able to direct proteins to mitochondria in the absence of endogenous TAZ. These peptides are not located within the predicted enzymatic clefts of TAZ, implying, without being bound by any one particular theory, that some BTHS disease causing mutations may affect mitochondrial localization without affecting transacylase activity. Since heart failure is known to be associated with various types of mitochondrial dysfunction (A. W. El-Hattab, et al., Mitochondrial Cardiomyopathies, Front Cardiovasc Med 3 (2016) 25), identification of mitochondrial targeting reagents may facilitate development of mitochondrially-targeted therapies for heart failure.

In this study, the internal sequences that are responsible for targeting TAZ to the mitochondria were investigated. Using various regions of TAZ fused with eGFP, two distinct fragments were found that were capable of localizing to mitochondria independently. TAZ (84-95) (LRHIWNLKLMRW (SEQ ID NO:33)) confers exclusive targeting to mitochondria of eGFP, while TAZ (185-220) (MSSEFLRFKWGIGRLIAECHLNPIILPLWHVGMNDV (SEQ ID NO:34)) results in partial targeting to mitochondria along with other subcellular compartments. The amino acid sequence of TAZ (SEQ ID NO:45) is shown in FIG. 9.

The acyltransferase TAZ is responsible for cardiolipin maturation in the mitochondrial inner membrane. TAZ is encoded in the nucleus and then targeted to the mitochondrial inner membrane, where its substrate is exclusively remodeled. Therefore, mislocalization of this protein, even if fully enzymatically active, could have severe implications for CL remodeling. It is thus critical to understand how TAZ is targeted to mitochondria. Targeting of proteins to mitochondria can be achieved with different types of targeting sequences, depending on the final destination and function of the protein. Whereas matrix proteins contain a cleavable N-terminal presequence that is recognized by the translocase of the outer membrane 20 (Tom20) complex, membrane and intermembrane space (IMS) proteins typically contain non-cleavable internal targeting sequences that are recognized by the Tom70/71 complexes (A. Chacinska, et al., Cell 138(4) (2009) 628-44). A subgroup of IMS and inner mitochondrial membrane (IMM) proteins are targeted to their correct location by further interactions with the mitochondrial intermembrane space assembly (MIA) complex, via a characteristic double cysteine (C) motif (typically in the form of $Cx_nC$) (J. Dudek, et al., Biochim Biophys Acta 1833(2) (2013) 274-85 and D. Stojanovski, et al., Biochim Biophys Acta 1783(4) (2008) 610-7). Mutations in these internal sequences could lead to aberrant sorting within the mitochondria, as well as failure to be targeted to the mitochondria at all. Human tafazzin contains one $Cx_3C$ motif located downstream of the 80-95 localization domain (GILKLRHIWNLKLMRW (SEQ ID NO:35)).

The mitochondrial localization sequences for TAZ were determined and it was found that there are two discrete regions that can target TAZ to the mitochondria. The two sequences, TAZ (84-95) and TAZ (185-220), are located in exons 3 and 7/8, respectively. While the exon 3 sequence targets TAZ exclusively to mitochondria, the exon 7/8 sequence does not confer precise localization. Both of these sequences are able to direct eGFP to mitochondria in the absence of wild type TAZ, in TAZ deficient cells. Although several BTHS-causing point mutations are located within these two regions, data shows that many of these mutations do not disrupt mitochondrial localization of the protein. This is in accordance with previous studies showing that most BTHS point mutations modeled in yeast do not lead to protein mislocalization, but rather are either catalytically null, or more labile and predisposed to degradation (K. Whited, et al., Human molecular genetics 22(3) (2013) 483-92).

As provided herein, TAZ contains two distinct mitochondria targeting regions. As the two mitochondrial localization sequences are able to independently target TAZ to the mitochondria, this suggests a redundant role for one of the peptides. TAZ (84-95) confers exclusive mitochondrial localization, indistinguishable from wild type TAZ, whereas TAZ (185-220) targets other sub-cellular compartments as well. The former sequence is unique and does not share homology with any other known proteins or mitochondrial localization sequences. The latter sequence may interact with other domains of the protein in the wild type molecule to form an exclusive mitochondrial targeting signal, or may be a remnant of an evolutionarily older signal. Of the four TAZ isoforms documented in humans, two lack exon 7, which encodes amino acids 181-195, part of the TAZ (185-220) peptide. Studies in 293 cells show these two isoforms are still able to localize to mitochondria, suggesting a redundant role for this peptide (Y. Xu, et al., The Journal of biological chemistry 284(42) (2009) 29230-9).

Exon 3 of TAZ plays an important role in mitochondrial localization. TAZ (84-95), the peptide responsible for exclusive mitochondrial localization, encompasses a large part of exon 3 of the TAZ gene. Recent in silico prediction of TAZ structure showed that most of this region is found on an exposed part of the globular protein structure and contains part of a patch of positive residues that help anchor it to the IMM in conjunction with the actual membrane insertion domain, predicted to reside in exon 1 (A. Hijikata, et al., Meta Gene 4 (2015) 92-106). R94, one of the sites most commonly found to have single point mutations leading to BTHS, is one of the residues that helps anchor TAZ to the membrane. Accordingly, it was surmised a mutation in this spot could lead to de-stabilization and mislocalization of the protein. In experiments, however, the TAZ R94S mutation did not affect mitochondrial localization of eGFP. This finding correlates with the ability of the TAZ (80-92) peptide (GILKLRHIWNLKL (SEQ ID NO:36)) to direct eGFP to the mitochondria. It is possible that TAZ R94S can still localize to mitochondria, but has difficulty remaining anchored to the IMM, where it needs to locate in order to interact with its substrate.

Both TAZ (80-92) and TAZ (84-95) are able to localize to the mitochondria, however, the overlapping sequence of 82-92 does not. The former two peptides contain a similar number of positively charged and hydrophobic amino acids. It has been proposed that mitochondrial targeting sequences consist of alpha helices enriched in positively charged and hydrophobic amino acids that bind the outer membrane translocases (J. Dudek, et al., Biochim Biophys Acta 1833 (2) (2013) 274-85 and Y. Abe, et al., Cell 100(5) (2000) 551-60). Without being bound by any one particular theory, structure in the form of a minimal length amphipathic helix may also be required, in addition to a specific amino acid sequence. This may explain why TAZ (82-92) is not able to localize eGFP to mitochondria, while the other two peptides are sufficient. It is also possible that the added amino acids provide essential post-translational modifications, which are not present in the shortened sequences.

In silico modeling of human TAZ structure: although the bulk of exon 3 is exposed, the in silico model locates the G80 and L82 residues in a secondary structure within the core of the protein. While it could be intuitively expected that a mitochondrial targeting sequence would need to be exposed to the surface of the protein for interaction with the TOM complex, a large number of proteins have been shown to enter mitochondria in an incompletely folded state, accompanied by chaperones on the cytosolic side (W. Neupert, et al., Annu Rev Biochem 76 (2007) 723-49). It is therefore possible, without being bound by any one specific theory, that a region normally buried within the core of the protein can serve as an organellar localization domain. Similarly, I209, L210, L212, H214, and G216, part of the TAZ (185-220) peptide, are also predicted to locate in the core of the protein. Therefore, the predicted model of TAZ structure represents an enzymatic steady state, rather than a dynamic, structure-shifting, mitochondrial targeting state.

Correlation of human and yeast TAZ mitochondrial localization studies: yeast studies have previously identified the membrane insertion domain to reside between amino acids 215-232 in Taz1p, corresponding to 201-219 in human TAZ (J. D. Herndon, et al., Eukaryot Cell 12(12) (2013) 1600-8). This domain, in conjunction with an N-terminus flanking sequence, 204-232 in Taz1p (192-219 in human TAZ) has been proposed to facilitate mitochondrial import. In agreement with the yeast TAZ study, it was found, as provided herein, that TAZ (185-220) is able to partially target eGFP to mitochondria. Any attempts to shorten this sequence, however, using either TAZ (185-195), TAZ (192-203), or TAZ (195-220), completely abolished mitochondrial targeting. Whereas in this study exon 3 of TAZ more precisely targets mitochondria, in the yeast studies, mitochondrial targeting of Taz1p lacking the 204-232 peptide, but containing exon 3 was completely abolished. These results indicate that Taz1p and human TAZ differ in their mitochondrial targeting mechanisms and lend support to the speculation that the 185-220 peptide in human TAZ is a remnant of an evolutionarily older signal.

Several other BTHS missense mutations (G197R, I209N, L210R, L212P, and H214R) are located within the TAZ (185-220) peptide. The role these mutations might play in the localization of the protein was investigated; however, none of these mutations affected mitochondrial localization of TAZ. This may be unsurprising; however, as experiments showed that the TAZ (84-95) peptide is able to independently confer mitochondrial localization. In previous experiments, where I209, L210, and L212 mutations were modeled in yeast, they were shown to localize to the mitochondrial matrix rather than the IMM or OMM. Failure to localize to the IMM is expected to prevent proper remodeling of MLCL and thus affect membrane curvature and respiratory complex assembly (M. Schlame, et al., Nat Chem Biol 8(10) (2012) 862-9 and D. Acehan, et al., Biophys J 100(9) (2011) 2184-92).

Herndon, et al. (Eukaryot Cell 12(12) (2013) 1600-8) reported that Taz1p does not require a membrane potential to translocate into mitochondria, as most inner membrane proteins do. Herndon, et al. found it requires both TOM20 and 70 receptors on the surface, but likely does not require TIM22 or 23. Taz1p seems to interact with Tim10p instead. Although, human TAZ contains the recognition motif ($Cx_3C$) for the MIA complex, it is further away from the identified mitochondrial targeting signals than in other MIA substrate proteins, suggesting it may not be functional. Recent studies have found that overexpression of mitochondrial translocation proteins can affect mitochondrial protein import, therefore it is possible that overexpression of TOM20-tdTomato in the experiments provided herein could interfere with the proper localization of TAZ (A. Chacinska, et al., Cell 120(6) (2005) 817-29 and M. Harner, et al., The EMBO journal 30(16) (2011) 3232-41). Another caveat with the study presented herein is that the eGFP moiety may also prevent complete translocation to the IMM. The use of human proteins in a rat cell line may also lead to subtle differences in mitochondrial localization due to variations in protein sequence.

TAZ-eGFP does not co-localize with peroxisomes or lysosomes. A great deal of evidence has accumulated demonstrating the dynamic interplay between different organelles in the cell. The connection between mitochondria and endoplasmic reticulum (ER) has long been established, but more recently mitochondria derived vesicles (MDVs) have been shown to mediate transport from mitochondria to both peroxisomes and lysosomes (A. Sugiura, et al., The EMBO journal 33(19) (2014) 2142-56). Peroxisomes are arguably closely related to mitochondria; these two organelles not only share biogenesis and division markers, but recent studies have shown that mitochondria are required for de novo synthesis of peroxisomes (A. Sugiura, et al., The EMBO journal 33(19) (2014) 2142-56). It has been postulated that MDVs populate newly formed peroxisomes with proteins and lipid products derived from mitochondria, in addition to facilitating transport of fatty acids and oxidized products (A. Mohanty, et al., Frontiers in physiology 4 (2013) 268). CL, which is synthesized in the mitochondria, but has been detected in the peroxisomes of yeast, could be one such candidate (T. Wriessnegger, et al., Biochim Biophys Acta 1771(4) (2007) 455-61). Functionally, both organelles perform β-oxidation of fatty acids and neutralize oxidized products (A. Sugiura, et al., The EMBO journal 33(19) (2014) 2142-56). The result provided herein, that TAZ-eGFP was not detected in peroxisomes indicates, without being bound by any one particular theory, that it is unlikely to be carried over to the peroxisomes via MDVs. TAZ is not normally detected in peroxisomes, despite MDVs having been shown to bud off regions of both inner and outer mitochondrial membranes for delivery to peroxisomes. It is possible that the domains of mitochondrial membrane targeted for peroxisomes are not those where TAZ tends to be enriched, or that TAZ is endogenously present in such low amounts it cannot be detected.

Lysosomes are responsible for degrading molecules taken up by the cell by endocytosis, as well as cytoplasmic proteins and organelles (such as mitochondria) via auto/mitophagy (C. Settembre, et al., Nature reviews 14(5) (2013) 283-96). In addition, MDVs have been shown to bud off damaged sections of mitochondria and transport them to lysosomes, thereby avoiding the more costly mitophagy. Overexpression of a membrane protein such as TAZ (or parts of it) could lead to the formation of aggregates, which would make the TAZ-eGFP provided herein a target for lysosomal degradation. In addition, the over-expression of TAZ-eGFP could affect mitochondrial health, therefore, making these organelles targets for autophagy. However, no TAZ-eGFP signal localized in lysosomes was observed.

Conclusions and Implications: identification of minimal, non-functional protein domains that promote mitochondrial targeting but do not affect mitochondrial import is useful for localization studies and for development of targeted mitochondrial therapies. Herein it has been demonstrated that a short 12 amino acid fragment of TAZ (84-95) is sufficient to target eGFP to mitochondria and thus can be used for such an application. The IMM in particular is the site of oxidative phosphorylation and location of many important components of the electron transport apparatus, many of which have been implicated in mitochondrial dysfunction in human disease (V. S. Dhillon, et al., Mutat Res Rev Mutat Res 759 (2014) 1-13). Development of a peptide reagent that facilitates the delivery of therapeutic molecules to the IMM may lead to development of novel therapies for mitochondrial diseases that result from respiratory dysfunction.

One aspect of the disclosure relates to a pharmaceutical composition including a mitochondria-targeting polypeptide. The pharmaceutical composition may further include a therapeutic agent coupled to or bound to the mitochondria-targeting polypeptide. Furthermore, the pharmaceutical composition may include a pharmaceutically acceptable carrier.

In some embodiments, the mitochondria-targeting peptide may include an amino acid sequence having at least 75%, 76%, 80%, 84%, 85%, 90%, 95%, or 100% sequence identity to hTAZ (80-92) GILKLRHIWNLKL (SEQ ID NO:36). In certain embodiments, the mitochondria-targeting peptide may include an amino acid sequence having at least 75%, 80%, 83%, 85%, 90%, 95%, or 100% sequence identity to hTAZ (84-95) LRHIWNLKLMRW (SEQ ID NO:33). In various embodiments, the mitochondria-targeting peptide may include an amino acid sequence having at least 75%, 80%, 81%, 85%, 87%, 90%, 93%, 95%, or 100% sequence identity to hTAZ (80-95) GILKLRHIWNLKLMRW (SEQ ID NO:35). In some embodiments, the mitochondria-targeting peptide may include an amino acid sequence having at least 75%, 77%, 80%, 83%, 85%, 86%, 88%, 90%, 91%, 94%, 95%, 97%, or 100% sequence identity to hTAZ (185-220)

(SEQ ID NO: 34)
MSSEFLRFKWGIGRLIAECHLNPIILPLWHVGMNDV.

The therapeutic agent may be covalently bound to the mitochondria-targeting polypeptide. In some embodiments, the therapeutic agent may be coupled to or bound to the mitochondria-targeting polypeptide via a linker. For example, the linker may include an exemplary linker as described in Bioconjugate Techniques, 3$^{rd}$ Edition (2013) by Greg T. Hermanson, which is hereby incorporated by reference in its entirety.

In certain embodiments, the linker may be an amino acid linker. The amino acid linker may include between one and 20, three and 17, five and 15, eight and 12, or any other suitable number of amino acids. The therapeutic agent may include a therapeutic polypeptide. In such an embodiment, the therapeutic polypeptide may be co-expressed with the mitochondria-targeting polypeptide. In various embodiments, the therapeutic agent may include catalase, superoxide dismutase, and/or any other suitable agent that improves or is configured to improve mitochondrial function.

Another aspect of the disclosure is directed to methods of treating a subject in need thereof. The method may include administering a therapeutically effective amount of a pharmaceutical composition as described above to the subject. In some embodiments, the subject may have an aging-related condition, heart failure, diabetes, myocardial infarction, acquired mitochondrial disorder, inherited mitochondrial disorder, and/or any other suitable condition.

The inherited mitochondrial disorder may include autosomal dominant optic atrophy (ADOA), Leber's hereditary optic neuropathy (LHON), LHON plus, Leigh syndrome, pyruvate dehydrogenase complex deficiency (PDCD), thymidine kinase 2 (TK2) deficiency, Alpers disease, Barth syndrome, a beta-oxidation defect, carnitine-acyl-carnitine deficiency, carnitine deficiency, a creatine deficiency syndrome, coenzyme Q10 deficiency, complex I deficiency, complex II deficiency, complex III deficiency, complex IV deficiency/COX deficiency, complex V deficiency, chronic progressive external ophthalmoplegia syndrome (CPEO), CPT I deficiency, CPT II deficiency, Kearns-Sayre syndrome (KSS), lactic acidosis, leukoencephalopathy with brain stem and spinal cord involvement and lactate elevation (LBSL—leukodystrophy), long-chain acyl-CoA dehydrogenase deficiency (LOAD), long-chain L-3 hydroxyacyl-CoA dehydrogenase deficiency (LCHAD), Luft disease, multiple acyl-CoA dehydrogenase (MAD) deficiency, medium-chain acyl-CoA dehydrogenase deficiency (MCAD), mitochondrial encephalomyopathy lactic acidosis and stroke-like episodes (MELAS), myoclonic epilepsy and ragged-red fiber disease (MERRF), mitochondrial recessive ataxia syndrome (MIRAS), a mitochondrial cytopathy, mitochondrial DNA depletion, mitochondrial encephalopathy, mitochondrial neurogastrointestinal encephalopathy syndrome (MNGIE), neuropathy, ataxia, and retinitis pigmentosa (NARP), Pearson syndrome, pyruvate carboxylase deficiency, pyruvate dehydrogenase deficiency, a POLG mutation, short-chain acyl-CoA dehydrogenase deficiency (SCAD), 3-hydroxyacyl-CoA dehydrogenase (HADH) deficiency, very-long-chain acyl-CoA dehydrogenase deficiency (VLCAD), Friedrich's ataxia, and/or any other suitable inherited mitochondrial disorder.

In certain embodiments, the pharmaceutical composition may reduce a pathological effect of symptom of the aging-related condition, heart failure, diabetes, myocardial infarction, inherited mitochondrial disorder, and/or the any other suitable disorder. Furthermore, the subject may be a human, a feline, a canine, a rodent, or any other suitable subject.

Another aspect of the disclosure is directed to use of a pharmaceutical composition as described above in the manufacture of a medicament for the treatment of an aging-related condition, heart failure, diabetes, myocardial infarction, acquired mitochondrial disorder, inherited mitochondrial disorder, and/or any other suitable condition.

Another aspect of the disclosure is directed to a pharmaceutical composition for the treatment of an aging-related condition, heart failure, diabetes, myocardial infarction, acquired mitochondrial disorder, inherited mitochondrial disorder, and/or any other suitable disorder. The pharmaceutical composition may be as described above.

Another aspect of the disclosure is directed to a pharmaceutical composition as described above for use in the treatment of an aging-related condition, heart failure, diabetes, myocardial infarction, acquired mitochondrial disorder, inherited mitochondrial disorder, and/or any other suitable disorder.

Another aspect of the disclosure is directed to methods of delivering a compound to one or more mitochondria. The method may include coupling the compound to a mitochondria-targeting polypeptide. Furthermore, the method may include contacting one or more cells with the mitochondria-targeting compound.

In some embodiments, the mitochondria-targeting peptide may include an amino acid sequence having at least 75%, 76%, 80%, 84%, 85%, 90%, 95%, or 100% sequence identity to hTAZ (80-92) GILKLRHIWNLKL (SEQ ID NO:36). In certain embodiments, the mitochondria-targeting peptide may include an amino acid sequence having at least 75%, 80%, 83%, 85%, 90%, 95%, or 100% sequence identity to hTAZ (84-95) LRHIWNLKLMRW (SEQ ID NO:33). In various embodiments, the mitochondria-targeting peptide may include an amino acid sequence having at least 75%, 80%, 81%, 85%, 87%, 90%, 93%, 95%, or 100% sequence identity to hTAZ (80-95) GILKLRHIWNLKLMRW (SEQ ID NO:35). In some embodiments, the mitochondria-targeting peptide may include an amino acid sequence having at least 75%, 77%, 80%, 83%, 85%, 86%, 88%, 90%, 91%, 94%, 95%, 97%, or 100% sequence identity to hTAZ (185-220)

(SEQ ID NO: 34)
MSSEFLRFKWGIGRLIAECHLNPIILPLWHVGMNDV.

The method of delivering a compound to one or more mitochondria may be performed in an experimental context (e.g., in a laboratory by a researcher). The one or more cells may be contacted with the mitochondria-targeting compound in vitro. For example, the mitochondria-targeting compound may be added to one or more cells being grown in culture (e.g., a cell culture). In certain embodiments, the one or more cells may be contacted with the mitochondria-targeting compound in vivo. For example, the mitochondria-targeting compound may be administered to a subject including cells such as a mouse, rat, cat, dog, and/or any other suitable subject.

The compound may be a therapeutic agent. For example, the therapeutic agent may be an experimental therapeutic agent. A researcher may be analyzing or testing the experiment therapeutic agent to determine its efficacy and/or possible use as a therapeutic agent. The experimental therapeutic agent may be covalently bound to the mitochondria-targeting polypeptide. In some embodiments, the experimental therapeutic agent may be coupled to or bound to the mitochondria-targeting polypeptide via a linker as discussed above.

In certain embodiments, the linker may be an amino acid linker. The amino acid linker may include between one and 20, three and 17, five and 15, eight and 12, or any other suitable number of amino acids. The experimental therapeutic agent may include a therapeutic polypeptide. In such an embodiment, the experimental therapeutic polypeptide may be co-expressed with the mitochondria-targeting polypeptide. In various embodiments, the experimental therapeutic agent can be an agent that may be suitable for use in the treatment of a condition, disease, or disorder associated with mitochondrial dysfunction.

Another aspect of the disclosure is directed to methods of preparing a compound for delivery to one or more mitochondria. The method may include coupling the compound to a mitochondria-targeting polypeptide as described above.

Another aspect of the disclosure is directed to methods of delivering a compound to one or more mitochondria. The method may include obtaining a mitochondria-targeting compound including a compound that is coupled to a mitochondria-targeting polypeptide as described above. Furthermore, the method may include contacting one or more cells (e.g., in vitro or in vivo) with the mitochondria-targeting compound.

Another aspect of the disclosure is directed to biological tracers. The biological tracer may include a mitochondria-targeting polypeptide. Furthermore, the biological tracer may include one or more labels coupled to the mitochondria-targeting polypeptide.

The label may include a radioactive label, fluorescent label, luminescent label, paramagnetic label, enzymatic label, electron dense label, and/or any other suitable label. The label may be coupled to the mitochondria-targeting polypeptide via a linker as discussed above. In some embodiments, the label may be covalently bound to the mitochondria-targeting polypeptide.

In some embodiments, the mitochondria-targeting peptide may include an amino acid sequence having at least 75%, 76%, 80%, 84%, 85%, 90%, 95%, or 100% sequence identity to hTAZ (80-92) GILKLRHIWNLKL (SEQ ID NO:36). In certain embodiments, the mitochondria-targeting peptide may include an amino acid sequence having at least 75%, 80%, 83%, 85%, 90%, 95%, or 100% sequence identity to hTAZ (84-95) LRHIWNLKLMRW (SEQ ID NO:33). In various embodiments, the mitochondria-targeting peptide may include an amino acid sequence having at least 75%, 80%, 81%, 85%, 87%, 90%, 93%, 95%, or 100% sequence identity to hTAZ (80-95) GILKLRHIWNLKLMRW (SEQ ID NO:35). In some embodiments, the mitochondria-targeting peptide may include an amino acid sequence having at least 75%, 77%, 80%, 83%, 85%, 86%, 88%, 90%, 91%, 94%, 95%, 97%, or 100% sequence identity to hTAZ (185-220)

```
                                         (SEQ ID NO: 34)
MSSEFLRFKWGIGRLIAECHLNPIILPLWHVGMNDV.
```

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Full Length TAZ Localizes to Mitochondria

Initial efforts to colocalize TAZ-eGFP fusion proteins with MITOTRACKER™ Red dye were unsatisfactory, due to bleeding of red signal into other organelles that likely resulted from toxicity. To investigate further the TAZ mitochondrial localization signal, organellar marker-tdTomato fusion proteins and TAZ-eGFP fusion protein were co-expressed. Control studies with eGFP or tdTomato alone did not affect Tom20 or TAZ-eGFP fusion protein localization to mitochondria (FIG. 1, panels A and B). A previous study reports that TAZ protein is embedded in mitochondrial membranes, facing the intermembrane space (Y. W. Lu, et al., Human molecular genetics 25(9) (2016) 1754-70). Both TAZ isoforms tested, the 292 amino acid TAZ full length (isoform 1) and the 262 amino acid TAZ Δ5 (isoform 2), localized to mitochondria when co-expressed with the fusion proteins Tim23-tdTomato and Tom20-tdTomato, mitochondrial markers of the inner or outer membrane, respectively (FIG. 1, panels C, D, G, and H). These data are consistent with a previous report using HA-tagged TAZ (Y. Xu, et al., The Journal of biological chemistry 284(42) (2009) 29230-9). Neither TAZ variant-eGFP fusion protein colocalized with peroxisomes or lysosomes when co-expressed with the organelle-specific markers PXMP2- and LAMP2b-tdTomato fusion proteins, respectively (FIG. 1, panels E and F). In agreement with previous studies, exon 5 does not affect the mitochondrial localization of TAZ (Y. Xu, et al., The Journal of biological chemistry 284(42) (2009) 29230-9). Therefore, isoform 2 was used to investigate the amino acid sequences necessary for mitochondrial localization, however, amino acid numbers and mutation positions are in accordance with isoform 1 length, as described in the BTHS human TAZ gene variants database (Barth Syndrome Foundation, available at https://www_barthsyndrome_org/research/tazdatabase_html (Accessed Jul. 15, 2017), (S. M. Kirwin, et al., Mol Genet Metab 111(1) (2014) 26-32).

Figure 2:
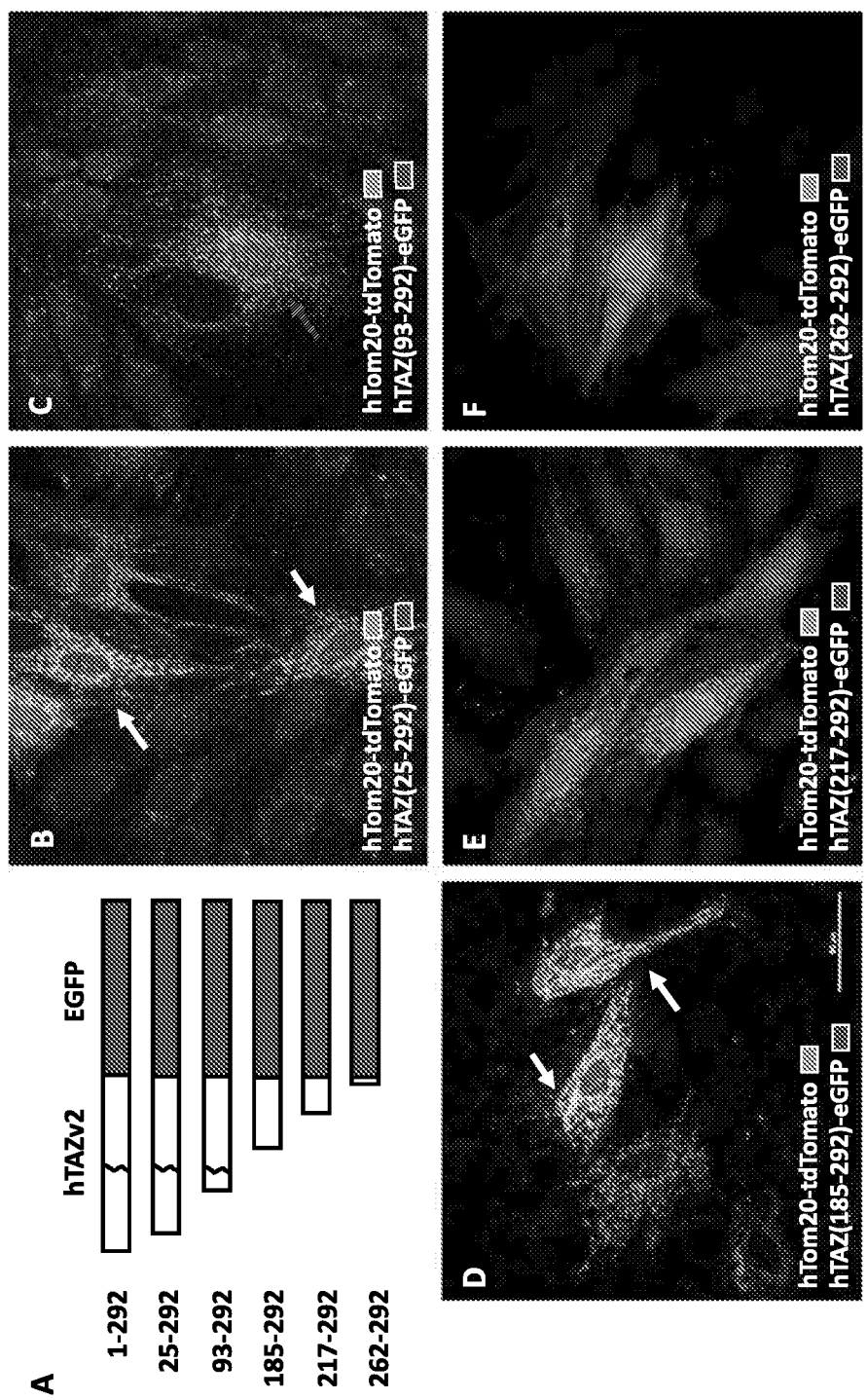
FIG. 2 shows mitochondrial localization of hTAZ isoform 2 serial N'-terminal deletion mutants. Panel A is a schematic diagram of hTAZ isoform 2 serial N'-terminal deletion mutants, which have no exon 5 encoding amino acids 124-154 (broken line). The amino acid numbers assigned by the full length hTAZ isoform 1 are listed on the left of each mutated TAZ fusion protein. The endogenous methionines in hTAZ were selected as initiation codons to create in-frame fusion proteins with eGFP. The maximal intensity projection of z-stack confocal images are shown for the mitochondrial outer membrane marker hTom20-tdTomato with hTAZ mutants: panel B, hTAZ(25-292); panel C, hTAZ(93-292); panel D, hTAZ(185-292); panel E, hTAZ(217-292); and panel F, hTAZ(262-292). All images were taken with a 60× oil lens and the white bar in panel D represents 50 μm.

Example 2—Mitochondrial Localization of N- and C-Terminus Truncated TAZ Fragments To identify TAZ mitochondrial localization peptides, a series of N- and C-terminus deletions of TAZ, in-frame with eGFP were made. For N-terminus deletions, the TAZ mutants were translated from endogenous methionines at M25, M93, M185, M217, and M262 as start codons (FIG. 2, panel A). The N-terminus deletion mutants TAZ (25-292) and TAZ (93-292) showed strong mitochondrial localization (FIG. 2, panels B and C), whereas TAZ (185-292) showed partial mitochondrial signal, along with some cytosolic signal (FIG. 2, panel D). Both TAZ (217-292) and TAZ (262-292) showed cytosolic signal only (FIG. 2, panels E and F), suggesting a potential mitochondrial targeting sequence between amino acids 185 and 217.

Figure 3:
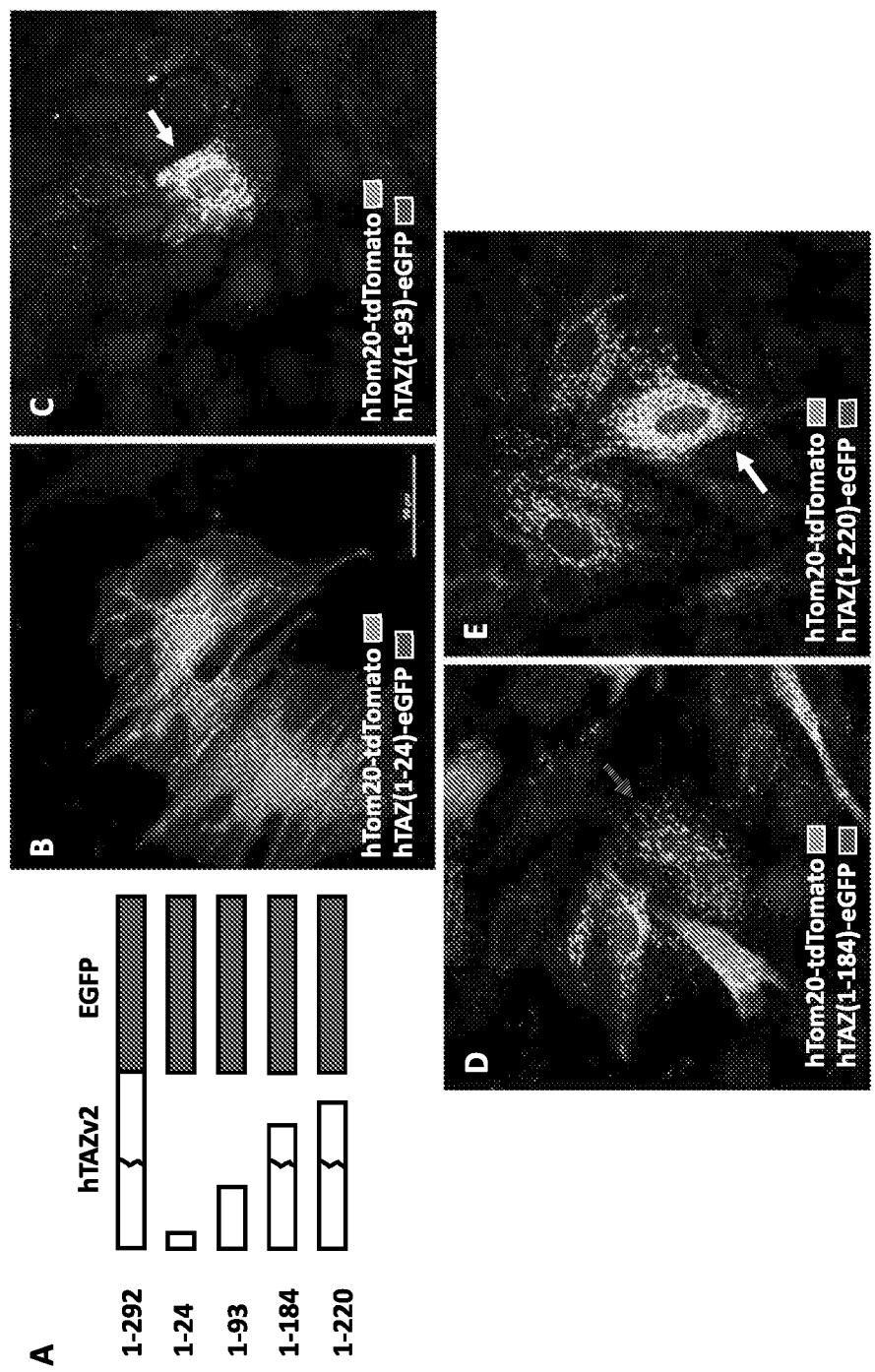
FIG. 3 shows mitochondrial localization of hTAZ isoform 2 serial C'-terminal deletion mutants. Panel A is a schematic diagram of hTAZ isoform 2 serial C'-terminal deletion mutants, which have no exon 5 encoding amino acids 124-154 (broken line). The amino acid numbers assigned by the full length hTAZ isoform 1 are listed on the left of each mutated TAZ. The peptide sequence gly-gly-gly was inserted as a linker at the C'-terminal TAZ deletion site in each clone to create an in-frame fusion protein with eGFP. The maximal intensity projection of z-stack confocal images are shown for the mitochondrial outer membrane marker hTom20-tdTomato with hTAZ mutants: panel B, hTAZ(1-24); panel C, hTAZ(1-93); panel D, hTAZ(1-184); and panel E, hTAZ(1-220). All images were taken with a 60× oil lens and the white bar in panel B represents 50 μm.

Four TAZ C-terminus deletions were also investigated (FIG. 3, panel A). TAZ (1-24) showed cytosolic eGFP signal (FIG. 3, panel B), whereas both TAZ (1-93) and (1-220) showed mitochondrial localization (FIG. 3, panels C and E). TAZ (1-184) showed some mitochondrial localization, but also significant cytosolic signal (FIG. 3, panel D). These results indicated that a TAZ mitochondrial localization signal lies between amino acids 25 and 220. Since both TAZ (1-93) and TAZ (185-292) showed some mitochondrial localization, it was investigated whether TAZ contains two mitochondrial localization signals: one in between amino acids 25-93 and the other between amino acids 185-220.

Figure 4:
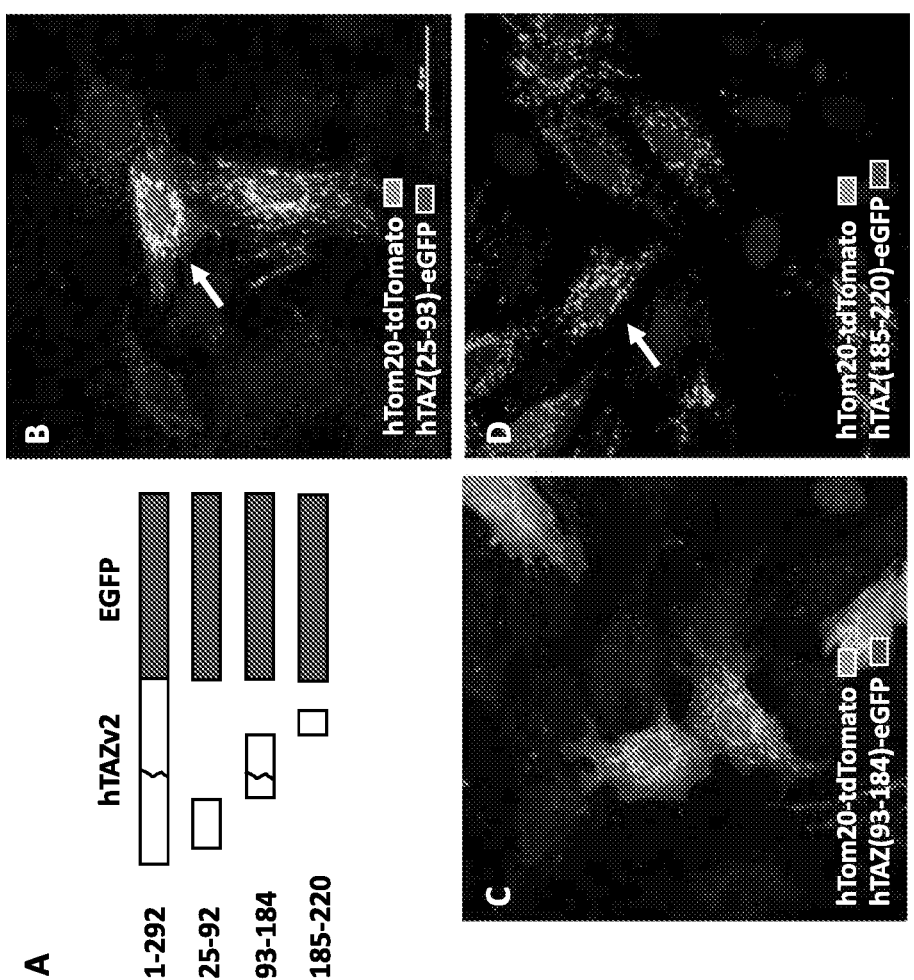
FIG. 4 shows mitochondrial localization of hTAZ isoform 2 subfragments. Panel A is a schematic diagram of hTAZ isoform 2 subfragments fused to eGFP. The peptide sequence gly-gly-gly was inserted as a linker at the C'-terminal TAZ deletion site when needed to create an in-frame fusion protein with eGFP. The maximal intensity projection of z-stack (0.2 mm×6 slices) confocal images are shown for the mitochondrial outer membrane marker hTom20-tdTomato with hTAZ mutants: panel B, hTAZ(25-92); panel C, hTAZ(93-184); and panel D, hTAZ(185-220). All images were taken with a 60× oil lens and the white bar in panel B represents 50 μm.

Example 3—TAZ Contains Two Distinct and Independent Mitochondrial Targeting Peptides To identify the possible mitochondrial localization signals in TAZ, the fragments encoding amino acids 25-92, 93-84, and 185-220 were isolated to generate plasmids encoding fusion proteins with eGFP (FIG. 4, panel A) and co-transfected these plasmids with the hTom20-tdTomato plasmid into H9c2 cells. Both TAZ (25-93) and TAZ (185-220) showed mitochondrial localization, with some cytosolic signal (FIG. 4, panels B and D). TAZ (93-184) localization is primarily cytosolic with a small fraction of signal present in mitochondria (FIG. 4, panel C). These results indicated that TAZ possesses two mitochondrial localization signals and each can function independently.

Figure 5:
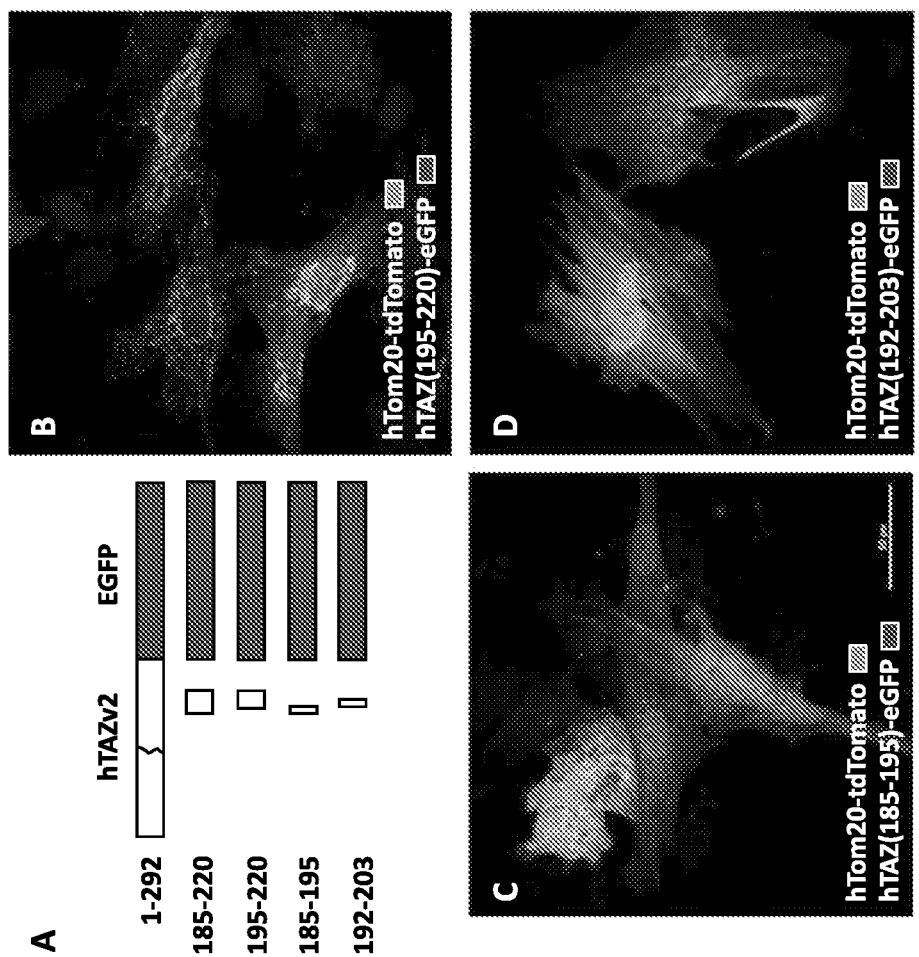
FIG. 5 shows mitochondrial localization of hTAZ isoform 2 subfragments derived from hTAZ(185-220). Panel A is a schematic diagram of hTAZ isoform 2 subfragments derived from hTAZ(185-220) fused to eGFP, which contain amino acids encoded from part of exon 7 (185-194) and entire exon 8 (195-215) and part of exon 9 (216-220). The peptide sequence gly-gly-gly was inserted as a linker at the C'-terminal TAZ deletion site to create an in-frame fusion protein with eGFP. The maximal intensity projection of z-stack (0.2 mm×6 slices) confocal images are shown for the mitochondrial outer membrane marker hTom20-tdTomato with hTAZ mutants: panel B, hTAZ(195-220); panel C, hTAZ(185-195); and panel D, hTAZ(192-203). All images were taken with a 60× oil lens and the white bar in panel C represents 50 μm.

Example 4—Fine Mapping of Essential TAZ Fragments that Confer Mitochondrial Localization TAZ (185-220) was further dissected into three smaller fragments: 185-195, 195-220, and 192-203, and eGFP fusion proteins were generated (FIG. 5, panel A). Interestingly, all of these smaller fragments were unable to direct the fusion protein to the mitochondria and were found only in the cytosol (FIG. 5, panels B, C, and D). These results indicated that the amino acids 185-220 are undividable and necessary for mitochondrial localization.

Figure 6:
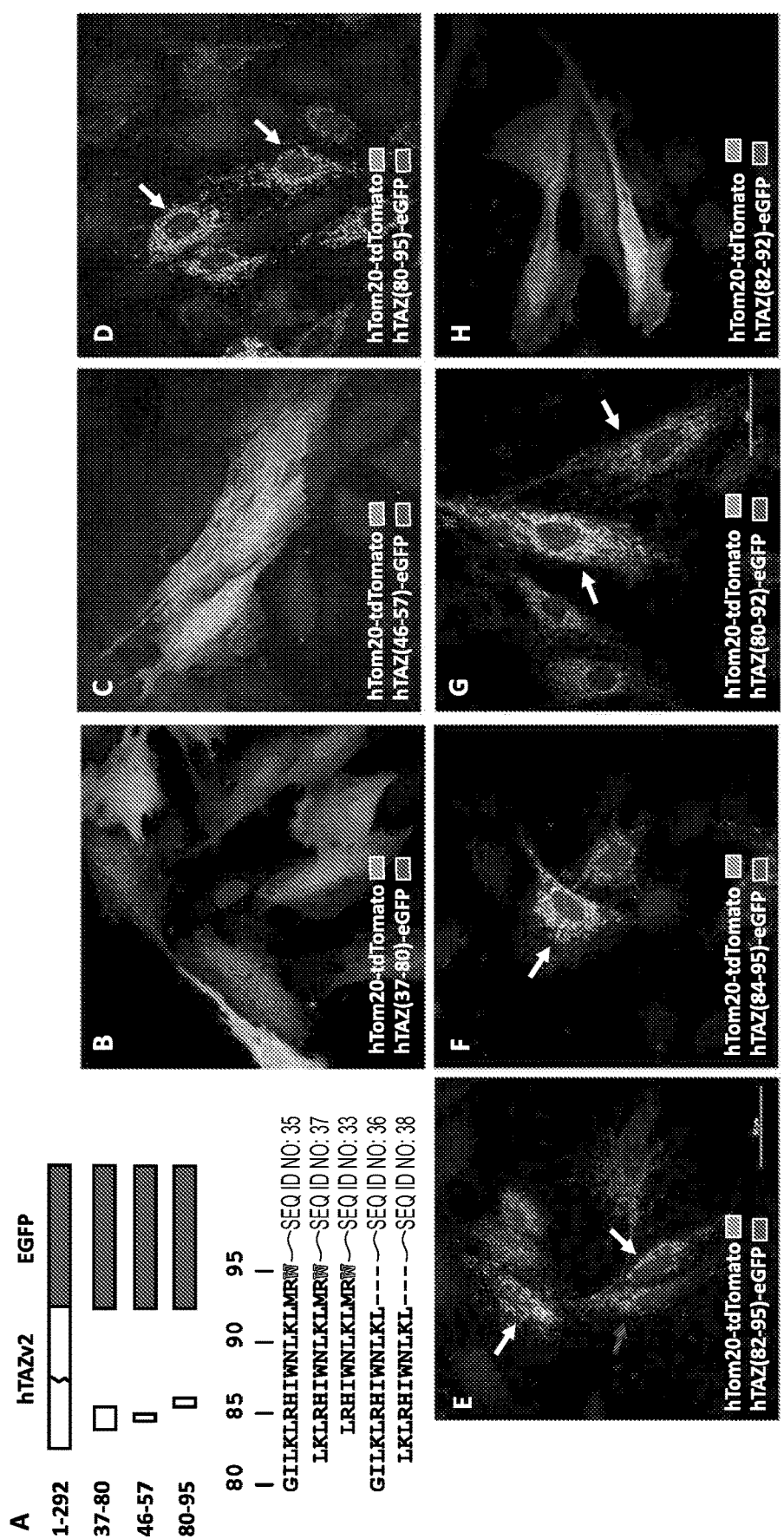
FIG. 6 shows mitochondrial localization of hTAZ isoform 2 subfragments derived from hTAZ(25-92). Panel A is a schematic diagram of hTAZ isoform 2 subfragments derived from hTAZ(25-92) fused to eGFP, which contain amino acids encoded from part of exon 1, exon 2 (37-80), and exon 3 (80-93). The amino acid sequence of hTAZ exon 3 is also shown. The splicing junction encodes the amino acid R94, which is a site of common missense mutations in Barth syndrome patients. The W95 residue encoded in exon 4 is indicated (outlined, no pattern letter). The peptide sequence gly-gly-gly was inserted as a linker at the C'-terminal TAZ deletion sites to create an in-frame fusion protein with eGFP. The maximal intensity projection of z-stack (0.2 mm×6 slices) confocal images are shown for the mitochondrial outer membrane marker hTom20-tdTomato with hTAZ mutants: panel B, hTAZ(37-80); panel C, hTAZ(46-57); panel D, hTAZ(80-95); panel E, hTAZ(82-95); panel F, hTAZ(84-95); panel G, hTAZ(80-92); and panel H, hTAZ(82-92). All images were taken with a 60× oil lens and the white bar in panel E represents 50 μm.

To narrow down the essential amino acid sequence required for mitochondrial localization, the TAZ (25-93) fragment was divided into smaller fragments (FIG. 6, panel A). Co-localization of hTom20-tdTomato and mutated TAZ fragment-eGFP proteins were analyzed in H9c2 cells by confocal microscopy. The N-terminus of this TAZ fragment, amino acids 37-80, which is encoded by exon 2, was mostly in the cytosol (FIG. 6, panel B). A computer predicted helix structure (A. Hijikata, et al., Meta Gene 4 (2015) 92-106) spanning amino acids 46-57 within this fragment does not confer mitochondrial localization (FIG. 6, panel C). In contrast, the other computer predicted helix (GOR4) at the C-terminus of this fragment, spanning amino acids 80-95, clearly possesses a mitochondrial targeting peptide (FIG. 6, panel D). To shorten the minimal amino acid sequence required to lead to mitochondrial localization of eGFP, the sequence was further narrowed down to: 82-95, 84-95, and 80-92. All three of these fragments still directed eGFP to mitochondria (FIG. 6, panels E, F, and G). It was attempted to further reduce the fragment, however, amino acid sequence 82-92 was unable to localize to mitochondria (FIG. 6, panel H). Taken together, but without being bound by any one particular theory, these results indicate that this region of TAZ contains an independent peptide responsible for mitochondrial localization, but the borders of this peptide appear to be inexact, which may be explained by secondary structure requirements. A basic local alignment search tool analysis against known proteins in the National Center for Biotechnology Information database (BLASTP) for the peptide sequence encompassing amino acids 80-95 revealed no homology to any known proteins other than tafazzin, demonstrating the novelty of this mitochondrial localization sequence.

Figure 7:
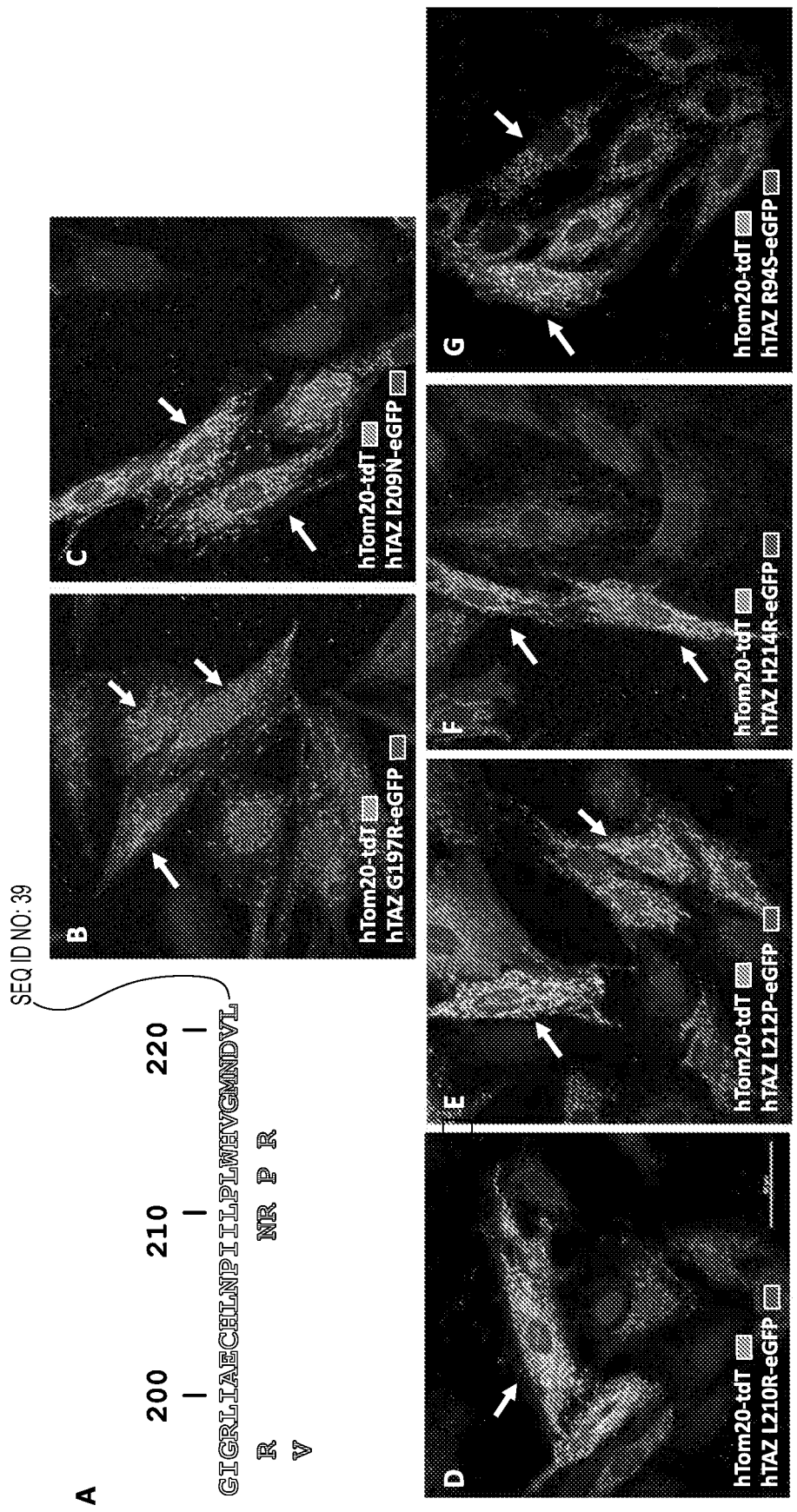
FIG. 7 shows mitochondrial localization of hTAZ-eGFP proteins containing Barth syndrome missense mutations. Panel A is an amino acid sequence of hTAZ exon 8 (outlined, no pattern letters) and 9 (outlined, angled pattern letters). The TAZ missense mutations in Barth syndrome are labeled in outlined, vertical pattern letters. Confocal images of TAZ mutants are shown: panel B, G197R; panel C, I209N; panel D, L210R, panel E, L212P; panel F, H214R; and panel G, R94S (located in exon 3). All images were taken with a 60× oil lens and the white bar in panel D represents 50 μm.

Example 5—Mitochondrial Localization of TAZ-eGFP Fusion Proteins Containing Barth Syndrome Missense Mutations Barth Syndrome missense mutations are located throughout the TAZ gene. To investigate whether known missense mutations in the identified localization peptides encoded by exon 3 or exon 8 would affect TAZ localization, selected TAZ mutations were engineered into the mitochondrially localizing eGFP fusion proteins and their localization was assessed. The TAZ Barth Syndrome mutations located in exon 8 were investigated by introducing these mutations into the full length hTAZ-eGFP fusion protein (FIG. 7, panel A). One of the hot spots for TAZ mutations is at G197. However, TAZG197R mutation does not affect mitochondrial localization. Similarly, the other mutations in exon 8, I209N, L210R, L212P, and H214R, also do not affect mitochondrial localization (FIG. 7, panels B, C, D, E, and F).

Another hot spot for mutation, R94, is located at the end of exon 3. Although mutations in the first or second nucleotides in the codon do not affect RNA splicing, the known mutated amino acids are relatively diverse and include cysteine, serine, histidine, leucine, or glycine. TAZ with the R94S mutation is still able to localize to mitochondria (FIG. 7, panel G).

Example 6—Localization of TAZ-eGFP in TAZ Knockout H9C2 Cells

Figure 8:
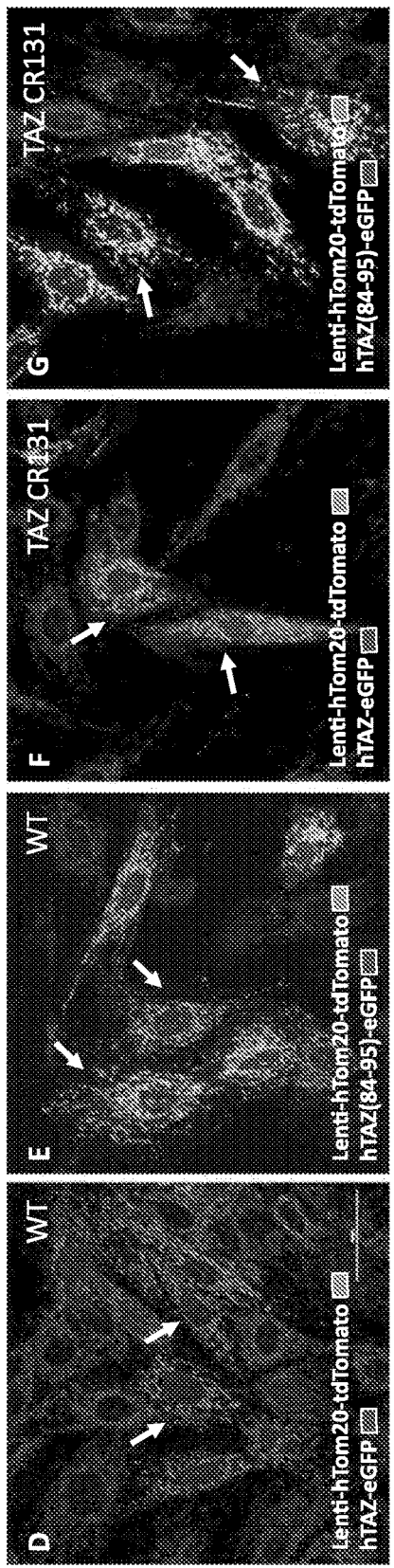
FIG. 8 shows TAZ-eGFP mitochondrial localization in H9c2 TAZ Knockout cells. Panel A depicts a strategy of TAZ knockout in H9c2 by two tracer-gRNAs. Anti-sense (outlined, angled pattern letters) and sense (outlined, horizontal pattern letters) guide RNAs target the 5'- and 3'-end of exon 3, respectively. Panel B is a sequence alignment of TAZ CRISPR mutations in targeted H9c2 cell lines derived from single colonies. The exon 3 encoded amino acids are indicated above the WT DNA sequence. Clone CR22 has deletions (dashed line) in both alleles: one with an 11 nt deletion and the other with a 12 nt deletion combined with a single nucleotide insertion (outlined, vertical pattern letter "G"). CR131 has a 29 nt deletion. Both KO clones contain out-of-frame nonsense mutations. Panel C is a TAZ western blot of WT H9c2 and H9c2-derived TAZ CRISPR knockout cells. Antibodies were used to detect TAZ and also the mitochondrial complex 2 marker SDHA. Panels D-G show mitochondrial localization of TAZ-eGFP proteins in WT and TAZ-KO cells containing a stable lentiviral-hTom20-tdtomato marker: panel D, hTAZ-eGFP in WT cells; panel E, hTAZ(84-95)-eGFP in WT cells, panel F, hTAZ-eGFP in KO cells; and panel G, hTAZ(84-95)-eGFP in KO cells. All images were taken with a 60× oil lens and the white bar in panel D represents 50 μm.

The exact mechanism by which TAZ is imported into mitochondria is still unknown. To exclude the possibility of homodimerization, whereby the TAZ fragment-eGFP fusion proteins are carried into the mitochondria by normal, endogenously expressed TAZ interacting with the fusion protein, localization of the previous constructs was verified in TAZ knockout (KO) H9c2 cells. As exon 3 was found to be responsible for mitochondrial localization, it was targeted for deletion in the myoblasts using CRISPR/Cas9 technology (FIG. 8, panel A). Three separate lines were selected: one line, CR38, does not contain a TAZ mutation and two lines that contain TAZ deletions that were verified by sequencing. The sequence alignments revealed that both deletion cell lines, CR22 and CR131, contain TAZ nonsense mutations by deletion of 11 and 29 nucleotides of exon 3, respectively (FIG. 8, panel B). To further confirm the protein expression in both cell lines, western blot analyses showed that TAZ proteins were detectable in the wild type and CR38 lines, but not in the nonsense clones CR22 and CR131 (FIG. 8, panel C).

To investigate whether TAZ isoform 2 or TAZ (84-95) targeting to mitochondria is mediated by endogenous wild type TAZ, cell lines derived from H9c2 wild type were created, CR22 and CR131, which constitutively expressed hTom20-tdTomato by lentiviral infection. Using these cell lines, it was found that TAZ-eGFP and TAZ (84-95)-eGFP are still able to localize to mitochondria in both the TAZ KO lines and the WT myoblasts (FIG. 8, panels D, E, F, and G). Similar results were observed with TAZ(185-220)-eGFP. These data suggest that the short mitochondrial targeting sequences in TAZ are sufficient to target proteins to mitochondria in the absence of full length TAZ.

The following materials and methods were used in the Examples described above.

DNA constructs: the tdTomato open reading frame (ORF) was isolated by PCR from pCAG-ChromsonR-tdTomato (ADDGENE plasmid #59169, N. C. Klapoetke, et al., Nat Methods 11(3) (2014) 338-46) and cloned into peGFP-N1 to replace the eGFP ORF. To construct expression plasmids encoding organelle-specific fluorescent markers that localize to lysosomes, peroxisomes, mitochondrial inner and outer membranes, the ORFs of LAMP2b (NP_054701.1), PXMP2 (NP_061133.1), TIMM23 (NP_006318.1), TOMM20 (NP_055580.1), and TAZ (isoform 1, NP_000107.1 and isoform 2, NP_851828.1), respectively, were isolated from 293T cell cDNA by PCR with corresponding primers. The ORFs of organelle-specific markers were cloned in-frame at the N-terminus of tdTomato at Bgl II and Sal I sites, driven by the CMV early promoter. The ORF of wild type TAZ was cloned into peGFP-N1 (CLONTECH™, Mountain View, Calif.) at Bgl II and Sal I sites to generate the TAZ full length phTAZv1-eGFP and the TAZ Δ5 isoform 2 phTAZ-eGFP.

For constructing the N-terminal deletion series of human TAZ-eGFP fusion proteins, endogenous codons encoding methionines as initiation codons were selected to create in-frame fusions with eGFP at Bgl II and Sal I sites. The C-terminal TAZ deletion series were generated by PCR using hTAZ-eGFP as template and a reverse primer complementary to TAZ to create TAZ C-terminal mutations; the forward primer encoded a linker peptide (Gly-Gly-Gly) between the TAZ fragment and eGFP. The PCR products were isolated, digested with Sal I and ligated for transformation into STBL3 bacteria. For generating the single point mutations of hTAZ-eGFP, recombinant DNAs were generated by PCR of plasmid phTAZ-eGFP with the mutated nucleotides in primers according to the BTHS human TAZ gene variants database (Barth Syndrome Foundation, available at https://www_barthsyndrome_org/research/tazdatabase_html (Accessed Jul. 15, 2017), (S. M. Kirwin, et al., Mol Genet Metab 111(1) (2014) 26-32).

To generate a plasmid for clustered, regularly interspaced, short palindromic repeat RNA-guided (CRISPR) targeting of TAZ in female rat cardiomyoblast H9c2 cells, two sets of primers for gRNA expression were used to target TAZ exon 3: 5'-TTTCAGGATCCCTACGAAAA-3' (SEQ ID NO:1) and 5'-CTGAAGTTGATGCGTTGGTG-3' (SEQ ID NO:2) and were both cloned into pSQT1313 for the gRNA multiplex expression.

Plasmid constructs were confirmed by sequencing (EUROFINS™, Louisville, Ky.).

Cell culture and cell transfection: rat cardiomyoblast H9c2 cells were cultured in 10% FBS/DMEM on a cover slide. For fluorescence colocalization experiments, H9c2 cells were seeded at 25,000 cells/well on a 12 mm diameter coverslide in a 24-well plate and allowed to attach overnight. Equal amounts of plasmid DNAs, encoding mutated- or full length hTAZ-eGFP and organelle-specific tdTomato, were used to transfect cells with LIPOFECTAMINE® 3000 (lipid nanoparticle-based transfection reagent) (THERMO FISHER SCIENTIFIC™, Waltham, Mass.) according to the manufacturer's instructions. Cells were harvested and fixed with 4% paraformaldehyde/PBS and mounted with DAPI-VECTASHIELD® (4',6-diamidino-2-phenylindole (DAPI) containing antifade mounting media) (VECTOR LABORATORIES™, Burlingame, Calif.) or DAPI FLUOROMOUNT-G® (4',6-diamidino-2-phenylindole (DAPI) containing antifade mounting media) (SOUTHERN BIOTECH™, Birmingham, Ala.).

Tafazzin CRISPR knockout cell lines: to generate female rat cardiomyoblast H9c2 Tafazzin (NM_001025748) knockout lines, a dimeric CRISPR RNA-guided FokI nuclease approach for genome editing was used (S. Q. Tsai, et al., Nat Biotechnol 32(6) (2014) 569-76). This strategy reduces the potential for off-target effects by fusing the dimerization-dependent FokI nuclease to a catalytically inactive Cas9 (dCas9) to induce double stranded DNA breaks. This approach requires two separate guide RNAs on opposing strands of DNA. The H9c2 cells were plated in a 24-well plate at a density of 25,000 cells/well and transfected with 250 ng of the plasmid pSQT-rTAZ-exon3 and 750 ng of pSQT1601-FokI-dCAS9 to create indels, and co-transfected with 80 ng pIRES-hrGFP-Neo or with 120 ng pLKO-scramble for cell selection, using LIPOFECTAMINE® 3000 (THERMO FISHER SCIENTIFIC™, Waltham, Mass.). Single colonies resistant to 500 µg/mL G418 for 7-days or 1 µg/mL puromycin for 2-days were screened by PCR with primers flanking rTAZ exon 3 in introns 2 and 3 (Table 1) which generated a 120 bp PCR product in wild type cells. To verify the TAZ alleles, the PCR products were resolved in 8% polyacrylamide (19:1 acrylamide:bisacrylaminde) in 0.5×TBE buffer. The PCR products from each colony were cloned into pJET1.2 (THERMO FISHER SCIENTIFIC™, Waltham, Mass.) and verified by sequencing (EUROFINS™, Louisville, Ky.). The candidate clones were further tested for the 10 most probable predicted off-targets (http://crispr_mit_edu) by PCR with 10 sets of primers (Table 1).

TABLE 1

Primers to Assess for CRISPR Off-Target Mutations in Rat H9c2 Cells

| chr | Position | Off-target sequence | Primer |
|---|---|---|---|
| 3 | 158982241 | 5'-CTGGAGTTGGTGTGTT GGTGAGG-3' (SEQ ID NO: 3) | 5'-ATCTGGGAGAAG ATTTGCC-3' (SEQ ID NO: 4) 5'-CAATCCAGTCAT CATCCCC-3' (SEQ ID NO: 5) |
| 4 | 157813433 | 5'-TTTCAGGATGATTACG AAAAAAG-3' (SEQ ID NO: 6) | 5'-GCACACTTCCAG GTCTTG-3' (SEQ ID NO: 7) 5'-TTCCTAGTCCTG GGGTTG-3' (SEQ ID NO: 8) |
| 4 | 159638475 | 5'-TTTCAGGATGATTACG AAAAAAG-3' (SEQ ID NO: 9) | 5'-GGAGGCAGAGAT GTGCTC-3' (SEQ ID NO: 10) 5'-GAAGTTGTGGCA GAAGG-3' (SEQ ID NO: 11) |
| 5 | 159545402 | 5'-CAGCAGCTGGTGCGTT GGTGGAG-3' (SEQ ID NO: 12) | 5'-GGCCCACCGGAT TCCAG-3' (SEQ ID NO: 13) 5'-GCGAATGTTTGC AAGACC-3' (SEQ ID NO: 14) |

TABLE 1-continued

Primers to Assess for CRISPR
Off-Target Mutations in Rat H9c2 Cells

| chr | Position | Off-target sequence | Primer |
|---|---|---|---|
| 5 | 170642529 | 5'-CTGAGGCTCATGCGTT GGTGTGG-3' (SEQ ID NO: 15) | 5'-CCCAGGCTCCAC TTTTAG-3' (SEQ ID NO: 16) 5'-GCTGGTACTCTG GGAGG-3' (SEQ ID NO: 17) |
| 7 | 27695381 | 5'-ATGAGGTGGATGTGTT GGTGAGG-3' (SEQ ID NO: 18) | 5'-TTATTGGCAACG TTTTAGGG-3' (SEQ ID NO: 19) 5'-AGAACTCTCGAT GGCCAC-3' (SEQ ID NO: 20) |
| 11 | 50427060 | 5'-TTGAAGGAAACCTACG AAAAAGG-3' (SEQ ID NO: 21) | 5'-AATGCAGTGCTA GCCAAG-3' (SEQ ID NO: 22) 5'-CAGCAACATCAT CTAGGG-3' (SEQ ID NO: 23) |
| 11 | 78928855 | 5'-TATCAGGATGCCTATG AAAAGGG-3' (SEQ ID NO: 24) | 5'-CAAGAACTTGAC AAACATCAAC-3' (SEQ ID NO: 25) 5'-CACAATTACATC TTTGAGG-3' (SEQ ID NO: 26) |
| 14 | 47547999 | 5'-TACCAAGATTCCTACG AAAATAG-3' (SEQ ID NO: 27) | 5'-AGATGTCATGAT AATGGC-3' (SEQ ID NO: 28) 5'-TTGATCCAAAAT GCATAGTTG-3' (SEQ ID NO: 29) |
| 14 | 76188503 | 5'-TAGCAGGATACATACG AAAAGAG-3' (SEQ ID NO: 30) | 5'-TCTCCCACATCC CATGGTG-3' (SEQ ID NO: 31) 5'-GCAAAGATTTGA ACAGATAAATTG-3' (SEQ ID NO: 32) |

Confocal microscopy: the confocal images were taken with a 60× oil lens under a NIKON® A1R confocal mounted on a NIKON® TiE inverted microscope. The images are shown with maximal intensity projection of z-planes.

Western Blotting: H9c2 cells were cultured to confluency in 15 centimeter plates. Cells were then collected by scraping and centrifuged at 600×g for 5 minutes and the pellet resuspended in mitochondria isolation buffer (250 mM sucrose, 10 mM Tris pH 7.4, 0.1 mM EDTA). Cells were homogenized in a glass dounce homogenizer until 90% of cells showed trypan blue staining (70 strokes). Homogenates were then spun at 600×g for 10 minutes to pellet nuclei and cell debris and then at 7,600×g to pellet the crude mitochondrial fraction. The pellet was re-suspended in radioimmunoprecipitation assay (RIPA) buffer (50 mM Tris, pH 7.4, 100 mM NaCl, 1% Triton X-100, 0.25% SDS) with protease inhibitor cocktail (SIGMA® P8340) added. Protein concentration was measured by Bradford assay and 20 micrograms of protein from each sample were resolved by SDS-PAGE (10%). Proteins were transferred onto nitrocellulose membranes, which were then probed with antibodies against succinate dehydrogenase (SDHA, MITOSCIENCES™) and TAZ (Y. W. Lu, et al., Human molecular genetics 25(9) (2016) 1754-70). The SDHA antibody was used at a dilution of 1:10,000 and the TAZ antibody was used at a dilution of 1:1,000. The membrane was then blotted with secondary antibodies horse anti-mouse and goat anti-rabbit IgG HRP-conjugates (CELL SIGNALING TECHNOLOGY®), both at 1:5,000 dilution). The membranes were incubated with enhanced chemiluminescence agents (PIERCE™) and analyzed by a CHEMIDOC™ Image System (BIO-RAD™).

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value, ±19% of the stated value, ±18% of the stated value, ±17% of the stated value, ±16% of the stated value, ±15% of the stated value, ±14% of the stated value, ±13% of the stated value, ±12% of the stated value, ±11% of the stated value, ±10% of the stated value, ±9% of the stated value, ±8% of the stated value, ±7% of the stated value, ±6% of the stated value, ±5% of the stated value, ±4% of the stated value, ±3% of the stated value, ±2% of the stated value, or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the description herein. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Ed. or a dictionary known to those of ordinary skill in the art, such as the Oxford Dictionary of Biochemistry and Molecular Biology (Ed. Anthony Smith, Oxford University Press, Oxford, 2004).

It will be apparent to those having skill in the art that many changes may be made to the details of the above-described embodiments without departing from the underlying principles of the invention. The scope of the invention is therefore defined by the following claims and their equivalents.

The invention claimed is:

1. A pharmaceutical composition comprising: a mitochondria-targeting polypeptide consisting of an amino acid sequence having at least 90% to the amino sequence of SEQ ID NO:33, SEQ ID NO:34, SEQ ID NO:35, or SEQ ID NO:36; and a therapeutic agent coupled to the mitochondria-targeting polypeptide.

2. The pharmaceutical composition of claim 1, wherein the amino acid sequence has at least 90% sequence identity to the amino acid sequence of SEQ ID NO:33, SEQ ID NO:35, or SEQ ID NO:36.

3. The pharmaceutical composition of claim 1, wherein the amino acid sequence has at least 90% sequence identity to the amino acid sequence of SEQ ID NO:34.

4. The pharmaceutical composition of claim 1, wherein the therapeutic agent is covalently bound to the mitochondria-targeting polypeptide.

5. The pharmaceutical composition of claim 1, wherein the therapeutic agent is coupled to the mitochondria-targeting polypeptide via a linker.

6. The pharmaceutical composition of claim 5, wherein the linker comprises between one and 20 amino acids.

7. The pharmaceutical composition of claim 1, wherein the therapeutic agent comprises a therapeutic polypeptide, and wherein the therapeutic polypeptide is co-expressed with the mitochondria-targeting polypeptide.

8. The pharmaceutical composition of claim 1, wherein the therapeutic agent comprises catalase, superoxide dismutase, or an agent that improves mitochondrial function.

9. The pharmaceutical composition of claim 1, further comprising a pharmaceutically acceptable carrier.

10. A method of treating a subject in need thereof, the method comprising: administering a therapeutically effective amount of a pharmaceutical composition to the subject, the pharmaceutical composition comprising: a mitochondria-targeting polypeptide consisting of an amino acid sequence having at least 90% to the amino sequence of SEQ ID NO:33, SEQ ID NO:34, SEQ ID NO:35, or SEQ ID NO:36; and a therapeutic agent coupled to the mitochondria-targeting polypeptide; wherein the subject has an aging-related condition, heart failure, diabetes, myocardial infarction, acquired mitochondrial disorder, or inherited mitochondrial disorder.

11. A method of delivering a therapeutic to a mitochondrion, the method comprising: coupling the therapeutic to a mitochondria-targeting polypeptide consisting of an amino acid sequence having at least 90% to the amino sequence of SEQ ID NO:33, SEQ ID NO:34, SEQ ID NO:35, or SEQ ID NO:36 to form a mitochondria-targeting therapeutic; and contacting a cell with the mitochondria-targeting therapeutic.

12. A method of preparing a therapeutic for delivery to a mitochondrion, the method comprising: coupling the therapeutic to a mitochondria-targeting polypeptide consisting of an amino acid sequence having at least 90% to the amino sequence of SEQ ID NO:33, SEQ ID NO:34, SEQ ID NO:35, or SEQ ID NO:36 to form a mitochondria-targeting therapeutic.

13. A method of delivering a therapeutic to a mitochondrion, the method comprising: obtaining a mitochondria-targeting therapeutic comprising a therapeutic that is coupled to a mitochondria-targeting polypeptide consisting of an amino acid sequence having at least 90% to the amino sequence of SEQ ID NO:33, SEQ ID NO:34, SEQ ID NO:35, or SEQ ID NO:36; and contacting a cell with the mitochondria-targeting therapeutic.

14. A biological tracer comprising: a mitochondria-targeting polypeptide consisting of an amino acid sequence having at least 90% to the amino sequence of SEQ ID NO:33, SEQ ID NO:34, SEQ ID NO:35, or SEQ ID NO:36; and a label coupled to the mitochondria-targeting polypeptide.

* * * * *

SEQUENCE LISTING

```
<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tttcaggatc cctacgaaaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctgaagttga tgcgttggtg                                                   20

<210> SEQ ID NO 3
<211> LENGTH: 23
<212> TYPE: DNA
<213> ORGANISM: Artificial Sequence
<220> FEATURE:
<223> OTHER INFORMATION: Off-target sequence
```

```
<400> SEQUENCE: 3
ctggagttgg tgtgttggtg agg                                           23

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
atctgggaga agatttgcc                                                19

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
caatccagtc atcatcccc                                                19

<210> SEQ ID NO 6
<211> LENGTH: 23
<212> TYPE: DNA
<213> ORGANISM: Artificial Sequence
<220> FEATURE:
<223> OTHER INFORMATION: Off-target sequence

<400> SEQUENCE: 6
tttcaggatg attacgaaaa aag                                           23

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gcacacttcc aggtcttg                                                 18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ttcctagtcc tggggttg                                                 18

<210> SEQ ID NO 9
<211> LENGTH: 23
<212> TYPE: DNA
<213> ORGANISM: Artificial Sequence
<220> FEATURE:
<223> OTHER INFORMATION: Off-target sequence

<400> SEQUENCE: 9
tttcaggatg attacgaaaa aag                                           23

<210> SEQ ID NO 10
<211> LENGTH: 18
```

```
<212> TYPE: DNA
<213> ORGANISM: Artificial Sequence
<220> FEATURE:
<223> OTHER INFORMATION: Primer

<400> SEQUENCE: 10
ggaggcagag atgtgctc                                                     18

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
gaagttgtgg cagaagg                                                      17

<210> SEQ ID NO 12
<211> LENGTH: 23
<212> TYPE: DNA
<213> ORGANISM: Artificial Sequence
<220> FEATURE:
<223> OTHER INFORMATION: Off-target sequence

<400> SEQUENCE: 12
cagcagctgg tgcgttggtg gag                                               23

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
ggcccaccgg attccag                                                      17

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
gcgaatgttt gcaagacc                                                     18

<210> SEQ ID NO 15
<211> LENGTH: 23
<212> TYPE: DNA
<213> ORGANISM: Artificial Sequence
<220> FEATURE:
<223> OTHER INFORMATION: Off-target sequence

<400> SEQUENCE: 15
ctgaggctca tgcgttggtg tgg                                               23

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
```

```
cccaggctcc acttttag                                            18

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
gctggtactc tgggagg                                             17

<210> SEQ ID NO 18
<211> LENGTH: 23
<212> TYPE: DNA
<213> ORGANISM: Artificial Sequence
<220> FEATURE:
<223> OTHER INFORMATION: Off-target sequence

<400> SEQUENCE: 18
atgaggtgga tgtgttggtg agg                                      23

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ttattggcaa cgttttaggg                                          20

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
agaactctcg atggccac                                            18

<210> SEQ ID NO 21
<211> LENGTH: 23
<212> TYPE: DNA
<213> ORGANISM: Artificial Sequence
<220> FEATURE:
<223> OTHER INFORMATION: Off-target sequence

<400> SEQUENCE: 21
ttgaaggaaa cctacgaaaa agg                                      23

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
aatgcagtgc tagccaag                                            18

<210> SEQ ID NO 23
<211> LENGTH: 18
<212> TYPE: DNA
<213> ORGANISM: Artificial Sequence
```

```
<220> FEATURE:
<223> OTHER INFORMATION: Primer

<400> SEQUENCE: 23
cagcaacatc atctaggg                                                  18

<210> SEQ ID NO 24
<211> LENGTH: 23
<212> TYPE: DNA
<213> ORGANISM: Artificial Sequence
<220> FEATURE:
<223> OTHER INFORMATION: Off-target sequence

<400> SEQUENCE: 24
tatcaggatg cctatgaaaa ggg                                            23

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
caagaacttg acaaacatca ac                                             22

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
cacaattaca tctttgagg                                                 19

<210> SEQ ID NO 27
<211> LENGTH: 23
<212> TYPE: DNA
<213> ORGANISM: Artificial Sequence
<220> FEATURE:
<223> OTHER INFORMATION: Off-target sequence

<400> SEQUENCE: 27
taccaagatt cctacgaaaa tag                                            23

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
agatgtcatg ataatggc                                                  18

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ttgatccaaa atgcatagtt g                                              21
```

-continued

```
<210> SEQ ID NO 30
<211> LENGTH: 23
<212> TYPE: DNA
<213> ORGANISM: Artificial Sequence
<220> FEATURE:
<223> OTHER INFORMATION: Off-target sequence

<400> SEQUENCE: 30
tagcaggata catacgaaaa gag                                              23

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
tctcccacat cccatggtg                                                   19

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
gcaaagattt gaacagataa attg                                             24

<210> SEQ ID NO 33
<211> LENGTH: 12
<212> TYPE: PRT
<213> ORGANISM: Homo sapiens

<400> SEQUENCE: 33

Leu Arg His Ile Trp Asn Leu Lys Leu Met Arg Trp
1               5                   10

<210> SEQ ID NO 34
<211> LENGTH: 36
<212> TYPE: PRT
<213> ORGANISM: Homo sapiens

<400> SEQUENCE: 34

Met Ser Ser Glu Phe Leu Arg Phe Lys Trp Gly Ile Gly Arg Leu Ile
1               5                   10                  15

Ala Glu Cys His Leu Asn Pro Ile Ile Leu Pro Leu Trp His Val Gly
            20                  25                  30

Met Asn Asp Val
        35

<210> SEQ ID NO 35
<211> LENGTH: 16
<212> TYPE: PRT
<213> ORGANISM: Homo sapiens

<400> SEQUENCE: 35

Gly Ile Leu Lys Leu Arg His Ile Trp Asn Lys Leu Met Arg Trp
1               5                   10                  15

<210> SEQ ID NO 36
<211> LENGTH: 13
<212> TYPE: PRT
```

<210> SEQ ID NO 36
<211> LENGTH: (not shown)
<212> TYPE: PRT
<213> ORGANISM: Homo sapiens

<400> SEQUENCE: 36

Gly Ile Leu Lys Leu Arg His Ile Trp Asn Leu Lys Leu
1               5                   10

<210> SEQ ID NO 37
<211> LENGTH: 14
<212> TYPE: PRT
<213> ORGANISM: Homo sapiens

<400> SEQUENCE: 37

Leu Lys Leu Arg His Ile Trp Asn Leu Lys Leu Met Arg Trp
1               5                   10

<210> SEQ ID NO 38
<211> LENGTH: 11
<212> TYPE: PRT
<213> ORGANISM: Homo sapiens

<400> SEQUENCE: 38

Leu Lys Leu Arg His Ile Trp Asn Leu Lys Leu
1               5                   10

<210> SEQ ID NO 39
<211> LENGTH: 27
<212> TYPE: PRT
<213> ORGANISM: Homo sapiens

<400> SEQUENCE: 39

Gly Ile Gly Arg Leu Ile Ala Glu Cys His Leu Asn Pro Ile Ile Leu
1               5                   10                  15

Pro Leu Trp His Val Gly Met Asn Asp Val Leu
            20                  25

<210> SEQ ID NO 40
<211> LENGTH: 70
<212> TYPE: DNA
<213> ORGANISM: Homo sapiens

<400> SEQUENCE: 40 ttccttttc gtagggatcc tgaaactccg ccacatctgg aacctgaagt tgatgcgttg     60
gtgaggaaga                                                          70

<210> SEQ ID NO 41
<211> LENGTH: 46
<212> TYPE: DNA
<213> ORGANISM: Homo sapiens

<400> SEQUENCE: 41
ggatcctgaa actccgccac atctggaacc tgaagttgat gcgttg                  46

<210> SEQ ID NO 42
<211> LENGTH: 35
<212> TYPE: DNA
<213> ORGANISM: Homo sapiens

<400> SEQUENCE: 42
ggatcctgaa actccgccac gaagttgatg cgttg                              35

<210> SEQ ID NO 43
<211> LENGTH: 35
<212> TYPE: DNA

-continued

<213> ORGANISM: Homo sapiens

<400> SEQUENCE: 43
ggatcgcaca tctggaacct gaagttgatg cgttg                35

<210> SEQ ID NO 44
<211> LENGTH: 17
<212> TYPE: DNA
<213> ORGANISM: Homo sapiens

<400> SEQUENCE: 44
ggatcctgaa tgcgttg                17

<210> SEQ ID NO 45
<211> LENGTH: 292
<212> TYPE: PRT
<213> ORGANISM: Homo sapiens

<400> SEQUENCE: 45

```
Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Ala Glu Phe Phe
        115                 120                 125

Gln Ala Glu Asn Glu Gly Lys Gly Val Leu Asp Thr Gly Arg His Met
    130                 135                 140

Pro Gly Ala Gly Lys Arg Arg Glu Lys Gly Asp Gly Val Tyr Gln Lys
145                 150                 155                 160

Gly Met Asp Phe Ile Leu Glu Lys Leu Asn His Gly Asp Trp Val His
                165                 170                 175

Ile Phe Pro Glu Gly Lys Val Asn Met Ser Ser Glu Phe Leu Arg Phe
            180                 185                 190

Lys Trp Gly Ile Gly Arg Leu Ile Ala Glu Cys His Leu Asn Pro Ile
        195                 200                 205

Ile Leu Pro Leu Trp His Val Gly Met Asn Asp Val Leu Pro Asn Ser
    210                 215                 220

Pro Pro Tyr Phe Pro Arg Phe Gly Gln Lys Ile Thr Val Leu Ile Gly
225                 230                 235                 240

Lys Pro Phe Ser Ala Leu Pro Val Leu Glu Arg Leu Arg Ala Glu Asn
                245                 250                 255
```

```
Lys Ser Ala Val Glu Met Arg Lys Ala Leu Thr Asp Phe Ile Gln Glu
            260                 265                 270

Glu Phe Gln His Leu Lys Thr Gln Ala Glu Gln Leu His Asn His Leu
            275                 280                 285

Gln Pro Gly Arg
    290
```